(12) United States Patent
Ricciardi et al.

(10) Patent No.: US 12,245,777 B2
(45) Date of Patent: Mar. 11, 2025

(54) GUIDE SYSTEMS AND METHODS FOR LAPIDUS FUSION

(71) Applicant: ARTHREX, INC., Naples, FL (US)

(72) Inventors: Giovanni Ricciardi, Munich (DE); Alyssa Morgan, Naples, FL (US); Chris Powell, Naples, FL (US); Thomas G. Harris, La Canada, CA (US); Casey W. Pyle, Camarillo, CA (US); Ernst Rachlitz, Gilching (DE)

(73) Assignee: ARTHREX, INC., Naples, FL (US)

( * ) Notice: Subject to any disclaimer, the term of this patent is extended or adjusted under 35 U.S.C. 154(b) by 327 days.

(21) Appl. No.: 17/890,407

(22) Filed: Aug. 18, 2022

(65) Prior Publication Data
US 2024/0058017 A1    Feb. 22, 2024

(51) Int. Cl.
*A61B 17/17*    (2006.01)
*A61B 17/72*    (2006.01)
*A61B 17/56*    (2006.01)

(52) U.S. Cl.
CPC .......... *A61B 17/1728* (2013.01); *A61B 17/72* (2013.01); *A61B 2017/565* (2013.01)

(58) Field of Classification Search
CPC ................................................. A61B 17/1728
See application file for complete search history.

(56) References Cited

U.S. PATENT DOCUMENTS

| | | | | |
|---|---|---|---|---|
| 4,565,191 A | * | 1/1986 | Slocum | A61B 17/15 606/87 |
| 4,627,425 A | * | 12/1986 | Reese | A61B 17/15 606/82 |
| 9,427,240 B2 | * | 8/2016 | Von Zabern | A61B 17/1637 |
| 9,545,276 B2 | | 1/2017 | Buchanan et al. | |
| 9,622,805 B2 | * | 4/2017 | Santrock | A61B 17/1682 |
| 10,064,631 B2 | | 9/2018 | Dacosta et al. | |
| 10,512,470 B1 | * | 12/2019 | Bays | A61B 17/68 |
| 10,575,862 B2 | | 3/2020 | Bays et al. | |
| 10,856,886 B2 | | 12/2020 | Dacosta et al. | |
| 11,058,546 B2 | | 7/2021 | Hollis et al. | |
| 2013/0190766 A1 | * | 7/2013 | Harris | A61B 17/15 606/87 |
| 2017/0020537 A1 | | 1/2017 | Tuten | |
| 2020/0015856 A1 | | 1/2020 | Treace et al. | |
| 2020/0253641 A1 | | 8/2020 | Treace et al. | |
| 2021/0085338 A1 | | 3/2021 | Dacosta et al. | |
| 2021/0282823 A1 | | 9/2021 | Day et al. | |
| 2021/0330335 A1 | | 10/2021 | Boffeli et al. | |
| 2021/0361330 A1 | | 11/2021 | McAleer et al. | |
| 2022/0117644 A1 | | 4/2022 | Santrock et al. | |

FOREIGN PATENT DOCUMENTS

WO    2021050207    3/2021

OTHER PUBLICATIONS

International Search Report for International Application No. PCT/US2023/030318 mailed Nov. 13, 2023.

* cited by examiner

*Primary Examiner* — Christian A Sevilla
(74) *Attorney, Agent, or Firm* — Carlson, Gaskey & Olds, P.C.

(57) ABSTRACT

This disclosure relates to systems and methods for repairing bone deformities. The systems may include one or more guides for positioning instruments relative to bones and/or joints.

22 Claims, 21 Drawing Sheets

GUIDE SYSTEMS AND METHODS FOR LAPIDUS FUSION

BACKGROUND

This disclosure relates to surgical devices and methods for repairing bone deformities associated with a joint.

A bunion deformity may occur along the foot of a patient. The deformity may be referred to as hallux valgus. A Lapidus procedure may be utilized to treat the bunion deformity. The procedure may include fusing the tarsometatarsal (TMT) joint between the first metatarsal bone and medial cuneiform. Cartilage may be removed from one or more of the bones. The bones may be repositioned to correct the deformity. A bone plate or fastener may be utilized to fix the bones for facilitating fusion between the bone surfaces.

SUMMARY

This disclosure relates to systems and methods for repairing bone deformities. The systems and methods may be utilized to remove tissue from one or more bones and/or surfaces along a joint. The systems may include one or more guides that may be utilized for positioning instruments relative to the bones and/or joint. The guides may include a cutting guide and a trajectory guide. The cutting guide may be utilized for restricting movement of a cutting instrument. The trajectory guide may be utilized for placement of a fixation element for securing adjacent bones along the joint.

A guide assembly for orthopaedic procedures disclosed herein may include a housing dimensioned to contact tissue, a drive shaft coupled to the housing, the drive shaft extending along a shaft axis, and a guide sleeve carried by the drive shaft. The guide sleeve may include a guide passage extending along a passage axis. The guide passage may be dimensioned to receive an instrument. The guide sleeve may be translatable along the shaft axis in response to rotation of the drive shaft. The guide sleeve may be pivotable about the shaft axis to sweep the passage axis along a guide plane.

A guide assembly for orthopaedic procedures disclosed herein may include a housing dimensioned to contact tissue. The housing may include a first slot extending along a slot axis. A carrier may be translatable along the slot axis. A guide sleeve may be pivotably coupled to the carrier. The guide sleeve may include a guide passage dimensioned to receive an instrument.

A guide system for preparation of surgical sites disclosed herein may include a cutting guide and targeting guide. The cutting guide may include a first housing dimensioned to contact tissue, a drive shaft coupled to the first housing, the drive shaft extending along a shaft axis, and a first guide sleeve carried by the drive shaft. The first guide sleeve may include a first guide passage extending along a passage axis and dimensioned to receive a cutting instrument. The first guide sleeve may be translatable along the shaft axis in response to rotation of the drive shaft. The first guide sleeve may be pivotable about the shaft axis to sweep the passage axis along a guide plane. The targeting guide may include a second housing dimensioned to contact tissue, a carrier captured in the second housing, and a second guide sleeve pivotably coupled to the carrier. The second guide sleeve may include a second guide passage dimensioned to receive a guide element insertable in bone.

Methods of performing an orthopaedic procedure may include positioning a cutting guide relative to a joint established by first and second bones. The cutting guide may include a drive shaft coupled to a first housing, the drive shaft extending along a shaft axis. A first guide sleeve may be carried by the drive shaft. The first guide sleeve may include a first guide passage extending along a first passage axis. Methods may include setting a position of the first guide sleeve relative to the first housing, which may include translating the first guide sleeve along the shaft axis in response to rotation of the drive shaft. Methods may include inserting a cutting instrument through the first guide passage. Methods may include sweeping the cutting instrument along a cutting plane to remove tissue from at least one of the first and second bones along the joint in response to pivoting the first guide sleeve about the shaft axis.

The present disclosure may include any one or more of the individual features disclosed above and/or below alone or in any combination thereof.

The various features and advantages of this disclosure will become apparent to those skilled in the art from the following detailed description. The drawings that accompany the detailed description can be briefly described as follows.

BRIEF DESCRIPTION OF THE DRAWINGS

Like reference numbers and designations in the various drawings indicate like elements.

DETAILED DESCRIPTION

Figure 1:
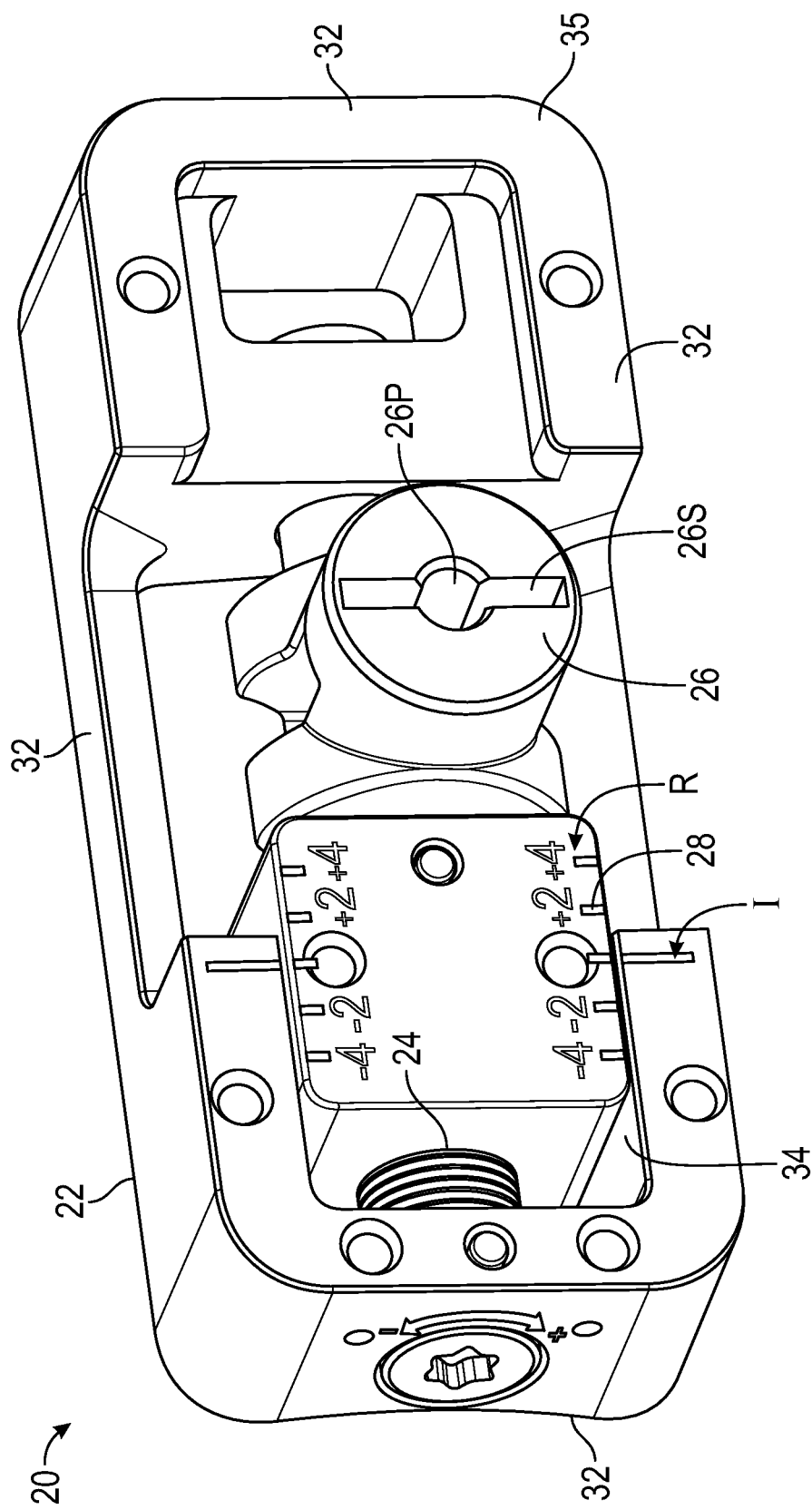
FIG. 1 illustrates a perspective view of a guide assembly.

This disclosure relates to surgical systems and methods for repairing bone deformities. The instrumentation and systems described herein may be utilized for dimensioning or otherwise preparing one or more bones at a surgical site, including resecting cartilage and other tissue along articular surfaces of an associated joint. In implementations, the disclosed systems and methods may be utilized in a Lapidus procedure for correcting a bunion deformity and may include fusing the tarsometatarsal (TMT) joint between the first metatarsal bone and medial cuneiform. The disclosed systems and methods may be utilized to perform an osteotomy along a bone at a position spaced apart from a joint.

The systems may include a cutting guide for guiding and restricting the path of a cutting instrument, such as a burr. The cutting guide may establish a reproducible means of resecting cartilage and other tissue along a joint. The cutting guide may include a moveable guide sleeve and guide block that may cooperate to provide a dual function. The surgeon may set a position of the guide sleeve for guiding a cutting instrument. The guide sleeve may be pivotable at the set position to sweep the cutting instrument along a resection plane for removing a determined amount of cartilage and other tissue from surfaces of the joint. The surgeon may set a position of the guide block to establish a determined amount of compression of the altered joint.

The systems may include a targeting guide for placing a fixation elements such as a compression screw to secure adjacent bones that establish a joint. The surgeon may position the targeting guide to substantially reestablish compression of a joint, such as a joint altered by the cutting instrument that may be guided by the cutting guide. The trajectory guide may include a guide sleeve for orienting the guide element relative to the bones and/or joint. The guide sleeve may be translated and/or rotated to establish a determined position and trajectory of a fixation element that may be utilized for placement of the fixation element across the compressed joint.

A position of each guide sleeve and guide block may be determined inter-operatively and/or pre-operatively and may be specified in a preoperative plan and may be set by articulating features of the respective guide. The techniques disclosed herein may be utilized to improve fusion of the joint surfaces, healing and mobility of the patient.

A guide assembly for orthopaedic procedures disclosed herein may include a housing dimensioned to contact tissue, a drive shaft coupled to the housing, the drive shaft extending along a shaft axis, and a guide sleeve carried by the drive shaft. The guide sleeve may include a guide passage extending along a passage axis. The guide passage may be dimensioned to receive an instrument. The guide sleeve may be translatable along the shaft axis in response to rotation of the drive shaft. The guide sleeve may be pivotable about the shaft axis to sweep the passage axis along a guide plane.

In implementations, the guide sleeve may include a guide slot extending along the guide plane. The guide slot may be dimensioned to receive an elongated instrument insertable into a joint.

In implementations, a guide block may be carried by the drive shaft. The guide block may include one or more block passages dimensioned to receive a respective fixation element.

In implementations, the guide sleeve and the guide block may be translatable along the shaft axis in response to articulation of a worm drive mechanism.

In implementations, the guide block and the guide sleeve may be translatable as a unit along the shaft axis in response to rotation of the drive shaft. The guide block may include sidewalls dimensioned to abut walls of the housing to limit rotation of the guide block about the shaft axis.

In implementations, the drive shaft may include a first shaft component and a second shaft component distributed along the shaft axis. The first shaft component may be fixed to the housing relative to the shaft axis and may be threadably connected to the guide block. The second shaft component may be slidably received in a bore of the first shaft component. The second shaft component may be fixed to the guide sleeve and the guide block relative to the shaft axis.

In implementations, the drive shaft may include a third shaft component extending along the shaft axis. The third shaft component may be fixed to the guide sleeve and may be slidably received in a bore extending through a wall of the housing.

In implementations, the instrument may establish a resection in bone at a position spaced apart from a joint in response to moving the instrument along the guide plane.

A guide assembly for orthopaedic procedures disclosed herein may include a housing dimensioned to contact tissue. The housing may include a first slot extending along a slot axis. A carrier may be translatable along the slot axis. A guide sleeve may be pivotably coupled to the carrier. The guide sleeve may include a guide passage dimensioned to receive an instrument.

In implementations, the guide passage may extend along a passage axis. The passage axis may extend through the first slot.

In implementations, a lock mechanism may include a pivot pin and a locking arm. The pivot pin may be received in a first bore of the carrier and a second bore of the guide sleeve. The guide sleeve may be pivotable about a pivot axis of the pivot pin. The locking arm may include a cam portion pivotably coupled to the pivot pin. The cam portion may be rotatable between an unlocked position and a locked position to move the pivot pin along the pivot axis such that the guide sleeve may bind against the housing to oppose relative movement.

In implementations, the housing may include a second slot extending outwardly from the first slot. The pivot pin may be translatable along the second slot to set a position of the carrier relative to the slot axis.

A guide system for preparation of surgical sites disclosed herein may include a cutting guide and targeting guide. The cutting guide may include a first housing dimensioned to contact tissue, a drive shaft coupled to the first housing, the drive shaft extending along a shaft axis, and a first guide sleeve carried by the drive shaft. The first guide sleeve may include a first guide passage extending along a passage axis and dimensioned to receive a cutting instrument. The first guide sleeve may be translatable along the shaft axis in response to rotation of the drive shaft. The first guide sleeve may be pivotable about the shaft axis to sweep the passage axis along a guide plane. The targeting guide may include a second housing dimensioned to contact tissue, a carrier captured in the second housing, and a second guide sleeve pivotably coupled to the carrier. The second guide sleeve may include a second guide passage dimensioned to receive a guide element insertable in bone.

In implementations, the first housing may include a first set of fixation passages. The second housing may include a second set of fixation passages. The first and second sets of fixation passages may be dimensioned to receive a common set of fixation elements insertable in bone.

In implementations, the first set of fixation passages may be arranged in a first spatial relationship. The second set of fixation passages may be arranged in a second spatial relationship that may substantially correspond to the first spatial relationship.

In implementations, the cutting guide may include a guide block carried by the drive shaft. The guide block may include a block passage dimensioned to receive a fixation element insertable in bone.

In implementations, the targeting guide may include a lock mechanism having a pivot pin and a locking arm. The second guide sleeve may be pivotable about a pivot axis of the pivot pin. The locking arm may include a cam portion pivotably coupled to the pivot pin. The cam portion may be rotatable to cause the pivot pin and the carrier to translate along the pivot axis such that the second guide sleeve may bind against the second housing.

Methods of performing an orthopaedic procedure may include positioning a cutting guide relative to a joint established by first and second bones. The cutting guide may include a drive shaft coupled to a first housing, the drive shaft extending along a shaft axis. A first guide sleeve may be carried by the drive shaft. The first guide sleeve may include a first guide passage extending along a first passage axis. Methods may include setting a position of the first guide sleeve relative to the first housing, which may include translating the first guide sleeve along the shaft axis in response to rotation of the drive shaft. Methods may include inserting a cutting instrument through the first guide passage. Methods may include sweeping the cutting instrument along a cutting plane to remove tissue from at least one of the first and second bones along the joint in response to pivoting the first guide sleeve about the shaft axis.

In implementations, the first guide sleeve may include a guide slot extending along the cutting plane. The step of positioning the cutting guide may include inserting an alignment tool through the guide slot and then into the joint prior to the step of translating the first guide sleeve.

In implementations, the first housing may include at least one fixation passage. The cutting guide may include a guide block having a block passage. Methods may include inserting a first fixation element through the at least one fixation passage and then into the first bone. Methods may include inserting a second fixation element through the block passage and then into the second bone. Methods may include translating the guide block along the shaft axis in response to rotating the drive shaft to cause the first and second fixation elements to compress the first and second bones against each other to establish a compressed state of the joint subsequent to the step of removing the tissue.

In implementations, the guide sleeve may include an access slot. Methods may include communicating a fluid stream through the access slot in a direction towards the cutting instrument.

In implementations, methods may include positioning a targeting guide relative to the joint subsequent to the step of removing the tissue. The targeting guide may include a carrier coupled to a second housing and a second guide sleeve pivotably coupled to the carrier at a pivot pin. The second guide sleeve may include a second guide passage. Methods may include setting a position of the second guide passage relative to the second housing, which may include translating the carrier relative to the second housing and pivoting the second guide sleeve about a pivot axis of the pivot pin. Methods may include inserting a guide element through the second guide passage and then across the joint. Methods may include moving a fastener along the guide element and then across the joint to fix a position of the first bone and the second bone relative to each other.

In implementations, the step of setting the position of the second guide passage may include translating the pivot pin along the pivot axis to cause the second guide sleeve to bind against the second housing in response to rotating a locking arm coupled to the pivot pin.

In implementations, the first housing may include a first set of fixation passages and a guide block having a block passage. Methods may include inserting a first fixation element through the block passage and then into the first bone. Methods may include inserting a second fixation element through a fixation passage of the first set of the fixation passages and then into the second bone. Methods may include translating the guide block along the shaft axis in response to rotation of the drive shaft to cause the first and second fixation elements to compress the first and second bones against each other to establish a compressed state of the joint.

In implementations, methods may include inserting a third fixation element through another fixation passage of the first set of fixation passages and then into the first bone in the compressed state. Methods may include removing the second fixation element from the guide block subsequent to the step of establishing the compressed state of the joint. Methods may include removing the cutting guide from the first fixation element and the third fixation element. The step of positioning the targeting guide may include substantially reestablishing the compressed state of the joint in response to inserting the first fixation element and the third fixation element through a second set of fixation passages of the second housing. The step of inserting the guide element across the joint may occur subsequent to the step of substantially reestablishing the compressed state of the joint.

In implementations, the joint may be a tarsometatarsal (TMT) joint.

Figure 2:
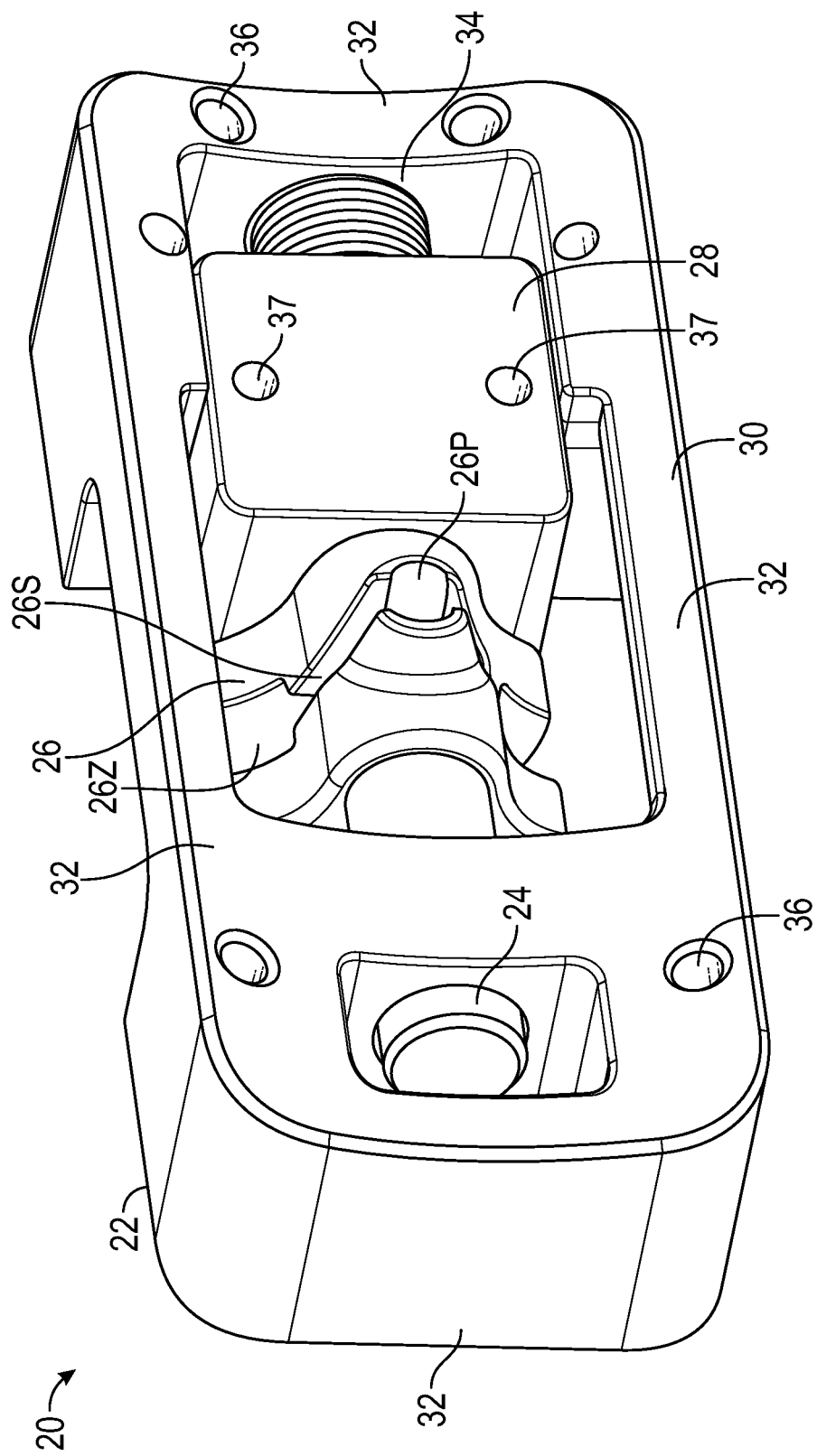
FIG. 2 illustrates another perspective view of the guide assembly of FIG. 1.

FIGS. 1 and 2 illustrate a first (e.g., cutting) guide assembly 20 according to an implementation. The guide assembly 20 may be utilized for an orthopedic procedure to treat one or more joints and bones. The guide assembly 20 may serve as a cutting guide for removing tissue from one or more bones, including cartilage and other tissue of adjacent bones establishing a joint. In implementations, the guide assembly 20 may be used in a Lapidus procedure to treat a bunion deformity (i.e., hallux valgus), which may include fusing the tarsometatarsal (TMT) joint between the first metatarsal bone and the medial cuneiform. The guide assemblies disclosed herein may be utilized to treat of other bones and joints, including other bones and joints of the foot, ankle, shoulder, hip and knee.

Figure 5:
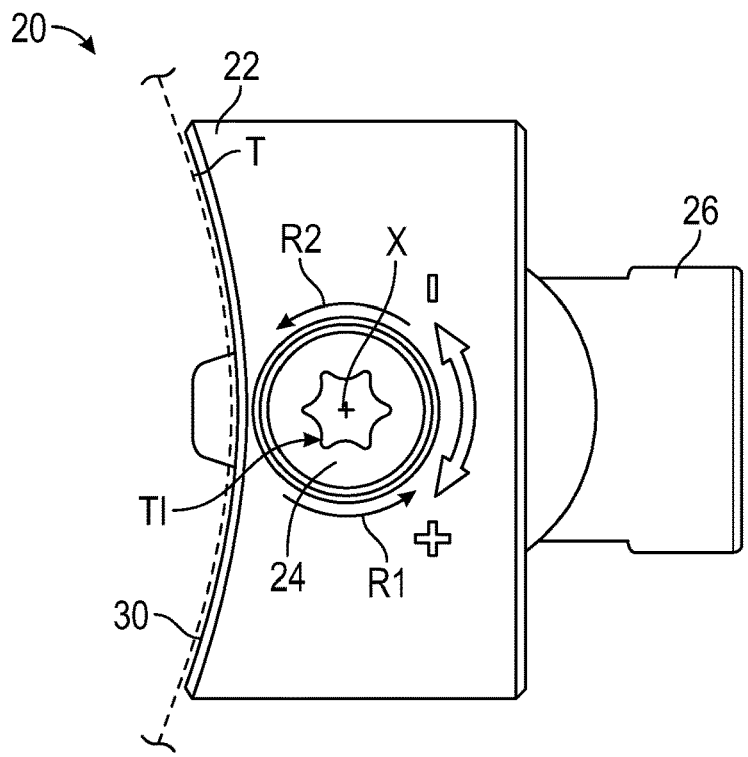
FIG. 5 illustrates an end view of the guide assembly taken along line 5-5 of FIG. 3.

The guide assembly 20 may include a (e.g., first) housing 22, a drive (e.g., guide) shaft 24, a (e.g., first) guide sleeve 26 and a guide block 28. In implementations, the guide block 28 may be omitted. The housing 22 may have a generally rectangular perimeter and may include an engagement face 30 (FIG. 2). The engagement face 30 of the housing 22 may be dimensioned to contact tissue adjacent to one or more bones of the joint. The engagement face 30 may have a generally concave geometry and may be dimensioned to seat against or otherwise contact tissue T adjacent to at least one, or more than one, bone (shown in dashed lines in FIG. 5). The surface of the tissue T may be adjacent to a non-articular surface and/or an articular surface of the respective bone and/or joint. The engagement face 30 may be dimensioned to sit on the tissue surface.

The housing 22 may include one or more walls 32. The walls 32 may be arranged to establish a perimeter having a generally rectangular geometry. The walls 32 may be arranged to establish a cavity 34. The cavity 34 may be dimensioned to extend between the engagement face 30 and a second face 35 (FIG. 1) on an opposite side of the housing 22.

The cavity 34 may be dimensioned to at least partially receive the guide sleeve 26 and guide block 28. The drive shaft 24 may be supported or otherwise coupled to the housing 22. The drive shaft 24 may be dimensioned to extend at least partially through the cavity 34.

Figure 3:
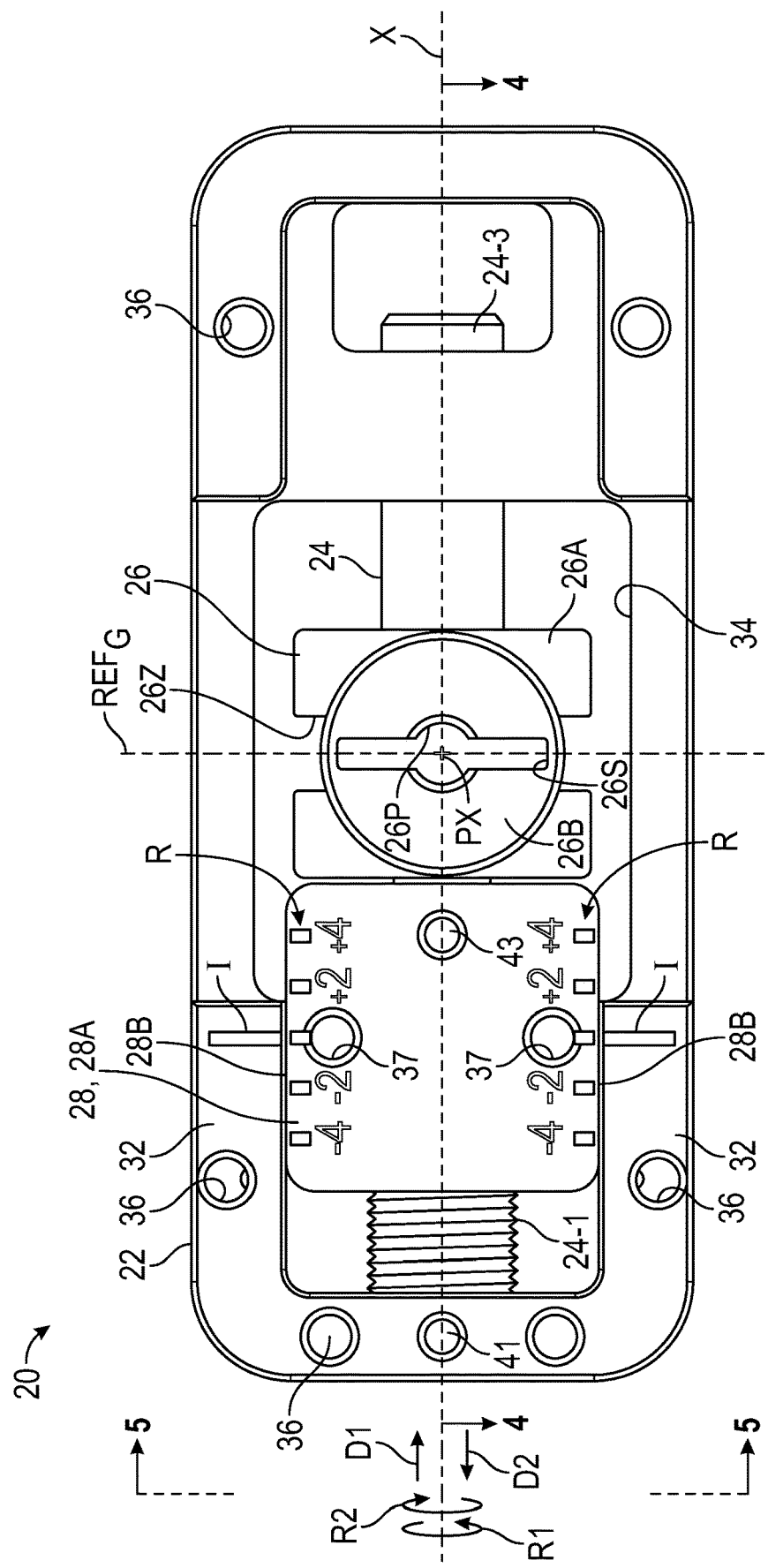
FIG. 3 illustrates a side view of the guide assembly of FIG. 1.
Figure 4:
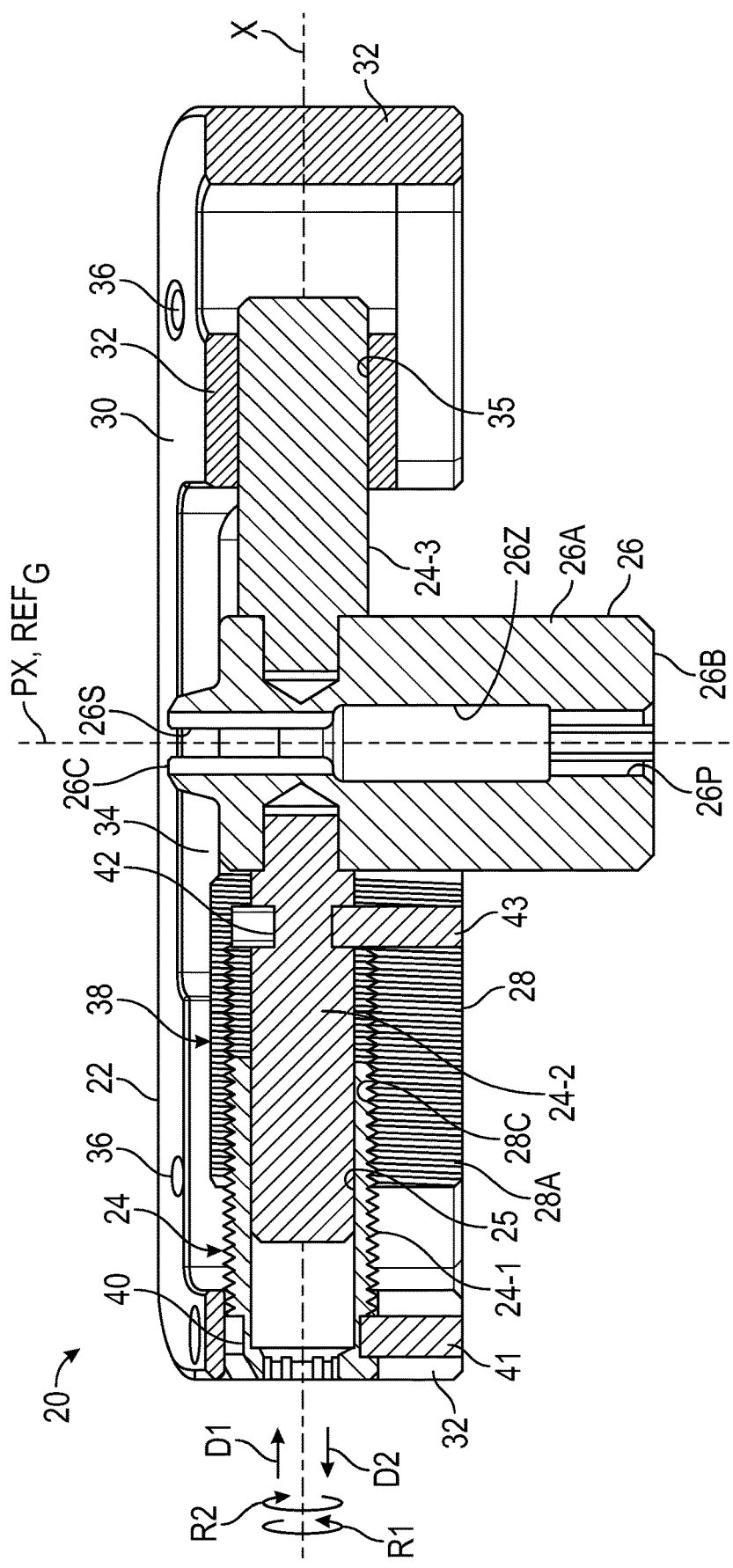
FIG. 4 illustrates a sectional view of the guide assembly taken along line 4-4 of FIG. 3.

Referring to FIGS. 3 and 4, with continuing reference to FIGS. 1 and 2, the guide sleeve 26 and/or guide block 28 may be carried by the drive shaft 24. The drive shaft 24 may include an elongated body extending along a shaft axis X. The guide sleeve 26 and guide block 28 may be distributed along the shaft axis X.

The housing 22 may include at least one or more fixation passages 36 (see also FIG. 2). In implementations, the housing 22 may include a first set of fixation passages 36 distributed along the perimeter of the housing 22. The fixation passages 36 may extend through a thickness of one or more walls 32 of the housing 22. Each of the fixation passages 36 may be dimensioned to receive a respective fixation element. The fixation elements may be insertable in bone. Various fixation elements may be utilized, such as k-wires, pins, screws, etc.

The guide sleeve 26 may include a sleeve body 26A extending between a first end 26B and a second end 26C. The guide sleeve 26 may include a (e.g., first) guide passage 26P and/or guide slot 26S (see also FIGS. 1-2). The guide passage 26P may extend along a passage axis PX. The guide slot 26S may extend along a guide (e.g., cutting or resection) plane $REF_G$. The guide passage 26P and guide slot 26C may be dimensioned to receive one or more instruments. Various instruments may be utilized, such as a rotatory cutting tool (e.g., burr), a reciprocating cutting tool (e.g., saw blade) or other cutting instrument, a punch, a fixation element, and/or a spacer or other tool for positioning the guide assembly 20 relative to a bone or joint. In implementations, the guide slot 26S may be dimensioned to receive an elongated instrument insertable into a joint for establishing a relative position of the guide assembly 20.

The guide passage 26P may be dimensioned such that the passage axis PX is established along the guide plane $REF_G$. In implementations, the guide plane $REF_G$ may be dimensioned to substantially bisect the sleeve body 26A. For purposes of this disclosure, the terms "substantially," "about" and "approximately" mean±10 percent of the stated value or relationship unless otherwise indicated. The guide plane $REF_G$ may establish a cutting plane for an instrument received in the guide passage 26P and/or the guide slot 26S (see, e.g., instrument T2 of FIG. 16). The guide slot 26S may be dimensioned to extend along the passage axis PX and the guide plane $REF_G$. The guide passage 26P may be dimensioned to extend between opposite sides of the guide slot 26S. A circumference of the guide passage 26P may be greater than a width of the guide slot 26S.

The guide assembly 20 may be adapted to cooperate with an irrigation system. The irrigation system may be configured to communicate a pressurized fluid (e.g., water) stream towards the surgical site. The irrigation system may be situated adjacent to the guide sleeve 26 (see, e.g., irrigation system S1 of FIGS. 16A and 16B). The guide sleeve 26 may include a second (e.g., access) slot 26Z. The slot 26Z may be transverse to, and may intersect, the guide slot 26S. The slot 26Z may extend between opposite sides of the sleeve body 26A and may establish a through passage for the fluid stream communicated from the irrigation system towards an instrument received in the guide passage 26P (see, e.g., instrument T2 of FIGS. 16A and 16B). In other implementations, the slot 26Z may be omitted.

The guide block 28 may include one or more block passages 37 (see also FIG. 2). Each of the block passages 37 may extend through a main body 28A of the guide block 28. Each of the block passages 37 may be dimensioned to receive a respective fixation element, including any of the fixation elements disclosed herein. The fixation elements may be insertable in bone to set a position of the guide block 28 relative to an adjacent bone or joint (see, e.g., fixation elements FE of FIG. 17).

The guide sleeve 26 and/or guide block 28 may be translatable along the shaft axis X to establish the position of the guide sleeve 26 and guide block 28 relative to the housing 22. Adjustment of the guide sleeve 26 and guide block 28 along the shaft axis X may be in discrete increments or may be continuously variable. The guide sleeve 26 and guide block 28 may be translatable as a unit along the shaft axis X in response to rotation of the drive shaft 24 about the shaft axis X. The guide sleeve 26 and guide block 28 may be translatable in a first direction D1 along the shaft axis X in response to rotation of the drive shaft 24 in a first rotational direction R1 (see also FIG. 5). The guide sleeve 26 and guide block 28 may be translatable in a second direction D2 along the shaft axis X in response to rotation of the drive shaft 24 in a second rotational direction R2 (see also FIG. 5). The first direction D1 may be opposed to the second direction D2. The first rotational direction R1 may be opposed to the second rotational direction R2. In implementations, the first rotational direction R1 may be a clockwise direction, and the second rotational direction R2 may be a counterclockwise direction, or vice versa.

The guide assembly 20 may include indicia for setting the position of the guide block 28 and/or guide sleeve 26. The indicia may include a ruler R and an indicator I adjacent to the ruler R (see, e.g., FIGS. 1 and 3). The ruler R may include increments associated with a range of positions of the guide block 28 and/or guide sleeve 26 along the drive axis X. The indicator I may be aligned with a selected position along the ruler R to establish a specified position of the guide block 28 and/or guide sleeve 26. The ruler R may be established along the guide block 28, and the indicator I may be established along the housing 22, although an opposite arrangement may be utilized. The indictor I may be aligned with a selected position along the ruler R in response to actuation of the drive shaft 24 to move the guide block 28 and/or guide sleeve 26 along the drive axis X.

The guide block 28 may include side walls 28B on opposite sides of the main body 28A (FIG. 3). The side walls 28B may be dimensioned to abut walls 32 of the housing 22 to limit rotation of the guide block 28 about the shaft axis X, including in the first and/or second rotational directions R1, R2.

The guide sleeve 26 may be pivotable about the shaft axis X of the drive shaft 24 to sweep or otherwise move the passage axis PX in an arc path along the guide plane $REF_G$. In implementations, the arc path may extend at least 10 degrees, or more narrowly at least 45 degrees but no more than 180 degrees, about the shaft axis X. The guide sleeve 26 may be dimensioned such that the guide plane $REF_G$ may be substantially perpendicular or otherwise transverse to the shaft axis X. The guide sleeve 26 may be translatable along the shaft axis X to set a position of the guide plane $REF_G$ relative to the shaft axis X. The guide sleeve 26 may be rotatable in the first and/or second rotational directions R1, R2.

Various techniques may be utilized to set a position and/or orientation of the guide sleeve 26 and/or guide block 28 relative to the housing 22. Referring to FIG. 4, with continuing reference to FIG. 3, the guide assembly 20 may include a worm drive mechanism 38 for moving the guide sleeve 26 and/or guide block 28. The drive shaft 24, guide sleeve 26 and guide block 28 may cooperate with the housing 22 to establish the worm drive mechanism 38. The guide sleeve 26 and/or guide block 28 may be translatable along the shaft axis X in response to articulation of the worm drive mechanism 38. In implementations, the drive shaft 24 may include a first shaft component 24-1, a second shaft component 24-2 and/or a third shaft component 24-3. The first, second, and/or third shaft components 24-1, 24-2, 24-3 of the drive shaft 24 may be dimensioned to extend along the shaft axis X. The shaft components 24-1, 24-2, 24-3 may be continuous or discontinuous and may be distributed along the shaft axis X.

An axial position of the first shaft component 24-1 may be fixed to the housing 22 relative to the drive axis X. The first shaft component 24-1 may include an annular groove 40. The annular groove 40 may be dimensioned to extend about a periphery of the first shaft component 24-1. The annular groove 40 may be dimensioned to receive a retention pin 41. The retention pin 41 may be secured to the housing 22 to fix a position of the first shaft component 24-1 relative to the shaft axis X. The retention pin 41 may be dimensioned to engage circumferential faces along the annular groove 40 to limit axial movement of the first shaft component 24-1 relative to the shaft axis X.

The first shaft component 24-1 of the drive shaft 24 may be at least partially received in a bore 28C of the guide block 28. In implementations, the first shaft component 24-1 may be threadably connected to the guide block 28. The periphery of the first shaft component 24-1 may include threads dimensioned to engage with threads along the bore 28C.

The second shaft component 24-2 of the drive shaft 24 may be slidable received in a bore 25 of the first shaft component 24-1. The bore 25 may extend along the shaft axis X. The second shaft component 24-2 of the drive shaft 24 may be fixed to the guide sleeve 26 and/or guide block 28 relative to the shaft axis X. Various techniques may be utilized to fix the second shaft component 24-2 to the guide sleeve 26 and/or guide block 28. In implementations, the second shaft component 24-2 may include an annular groove 42 established about a periphery of the second shaft component 24-2. The annular groove 42 may be dimensioned to receive a retention pin 43. The retention pin 43 may be secured to the guide block 28 to fix an axial position of the guide block 28 relative to the second shaft component 24-2. The retention pin 43 may be dimensioned to engage circumferential faces along the annular groove 42 to limit axial movement of the second shaft component 24-2 relative to the guide block 28. The second shaft component 24-2 may be rotatable relative to the guide block 28.

The third shaft component 24-3 may be fixed to the guide sleeve 26. The third shaft component 24-3 may be slidably received in a bore 35 of the housing 22. The bore 35 may extend through one of the walls 32 of the housing 22. The guide sleeve 26 may be arranged to interconnect or otherwise couple the second shaft component 24-2 and third shaft component 24-3 to establish the drive shaft 24. The guide sleeve 26 may be fixedly attached or otherwise secured to the second and third shaft components 24-2, 24-3 to limit relative axial and/or rotational movement with respect to the drive axis X. Various techniques may be utilized to fixedly attach or otherwise secure the guide sleeve 26 to the second and third shaft components 24-2, 24-3, such as welding, bonding and/or fixation with one or more fasteners. In other implementations, the second and third shaft components 24-2, 24-3 are an integrally formed to establish a single component that may extend through the guide sleeve 26.

Figure 6:
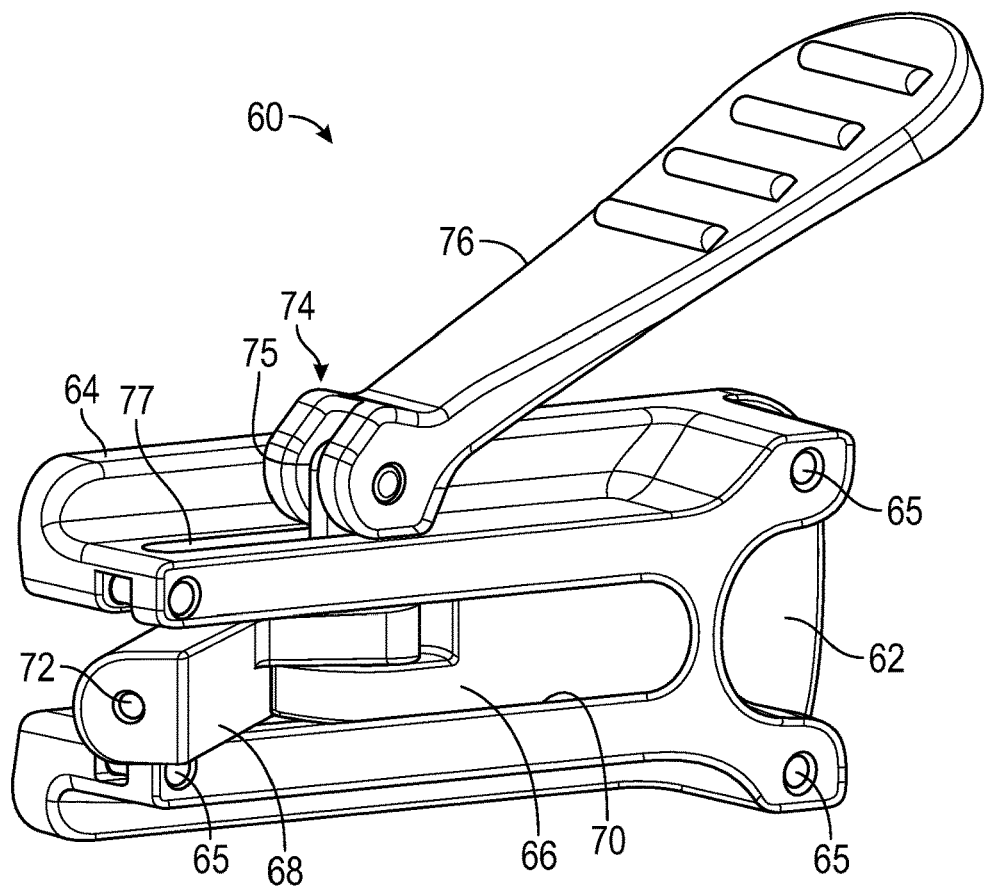
FIG. 6 illustrates a perspective view of another guide assembly.
Figure 7:
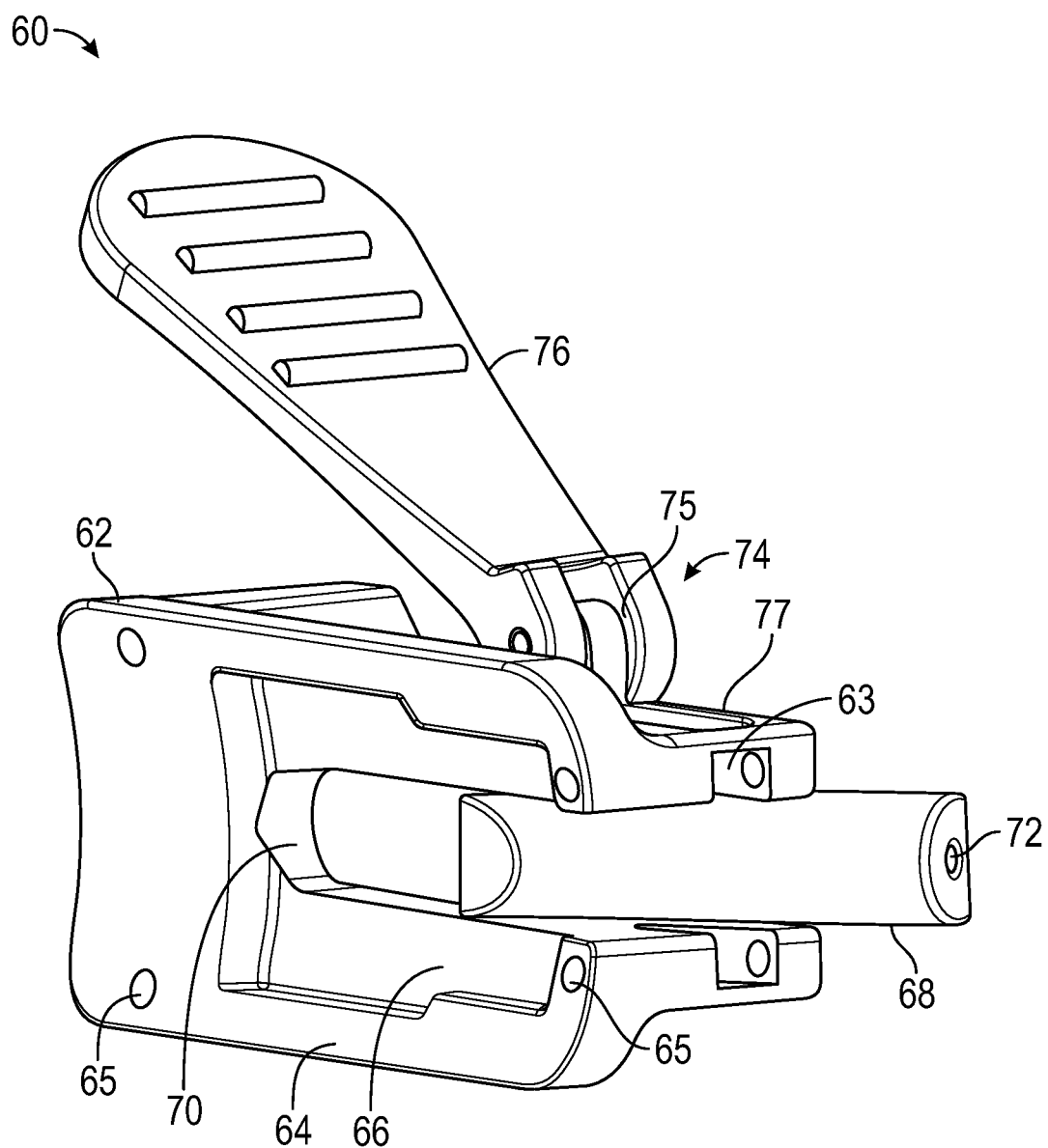
FIG. 7 illustrates another perspective view of the guide assembly of FIG. 6.

FIGS. 6 and 7 illustrate a second (e.g., targeting) guide assembly 60 according to an implementation. The guide assembly 60 may be utilized for an orthopedic procedure to treat one or more joints and bones, including any of the procedures, joints and bones disclosed herein such as a Lapidus procedure. The guide assembly 60 may serve to place one or more instruments relative to one or more joints and bones, such as any of the fixation and guide elements disclosed herein. The guide assemblies 20, 60 may be utilized independently or together to establish a guide system for preparation of a surgical site. The guide assemblies 20, 60 may be provided to the surgeon as a kit. The guide assemblies disclosed herein, including the guide assemblies 20 and/or 60, may be utilized to perform an osteotomy along a bone at a position spaced apart from a joint.

The guide assembly 60 may include a (e.g., second) housing 62. The housing 62 may include an engagement face 64 (FIG. 7). The engagement face 64 may be dimensioned to contact tissue adjacent to one or more bones. The engagement face 64 may have a generally concave geometry and may be dimensioned to seat against or otherwise contact tissue adjacent to at least one, or more than one, bone (see, e.g., tissue T of FIG. 5). The surface of the tissue may be adjacent to a non-articular surface and/or an articular surface of the respective bone. In implementations, the engagement face 64 may have a curvature that is substantially equal to a curvature of the engagement face 30 of the first guide assembly 20 (see, e.g., FIG. 5).

The housing 62 may include one or more fixation passages 65. In implementations, the housing 62 may include a set of fixation passages 65 distributed along the perimeter of the housing 62. Each of the fixation passages 65 may be dimensioned to receive a respective fixation element insertable in bone, including any of the fixation elements disclosed herein (see, e.g., FIG. 21).

Figure 19:
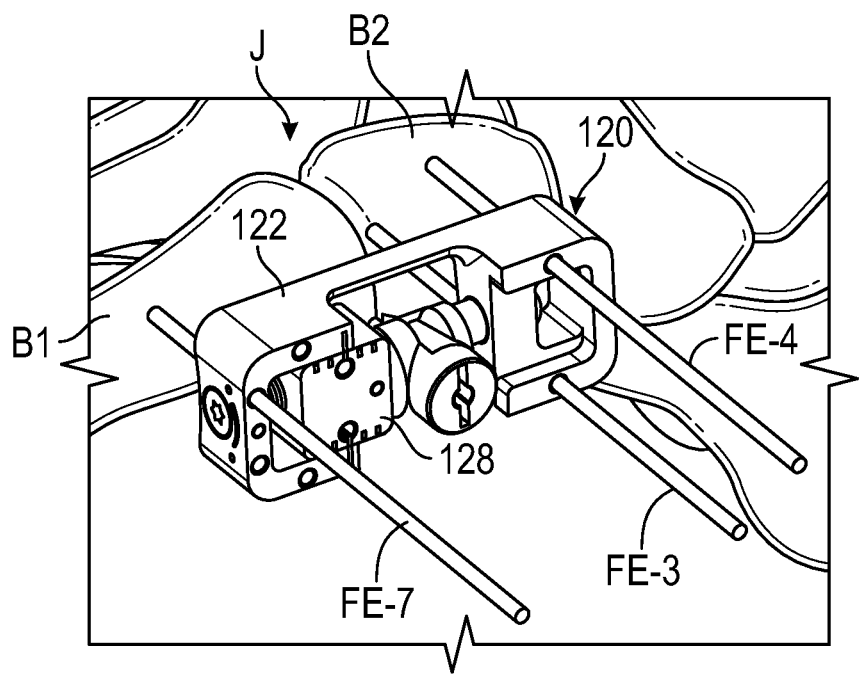
FIG. 19 illustrates removal of the fixation elements from the guide block of the guide assembly of FIG. 18.
Figure 21:
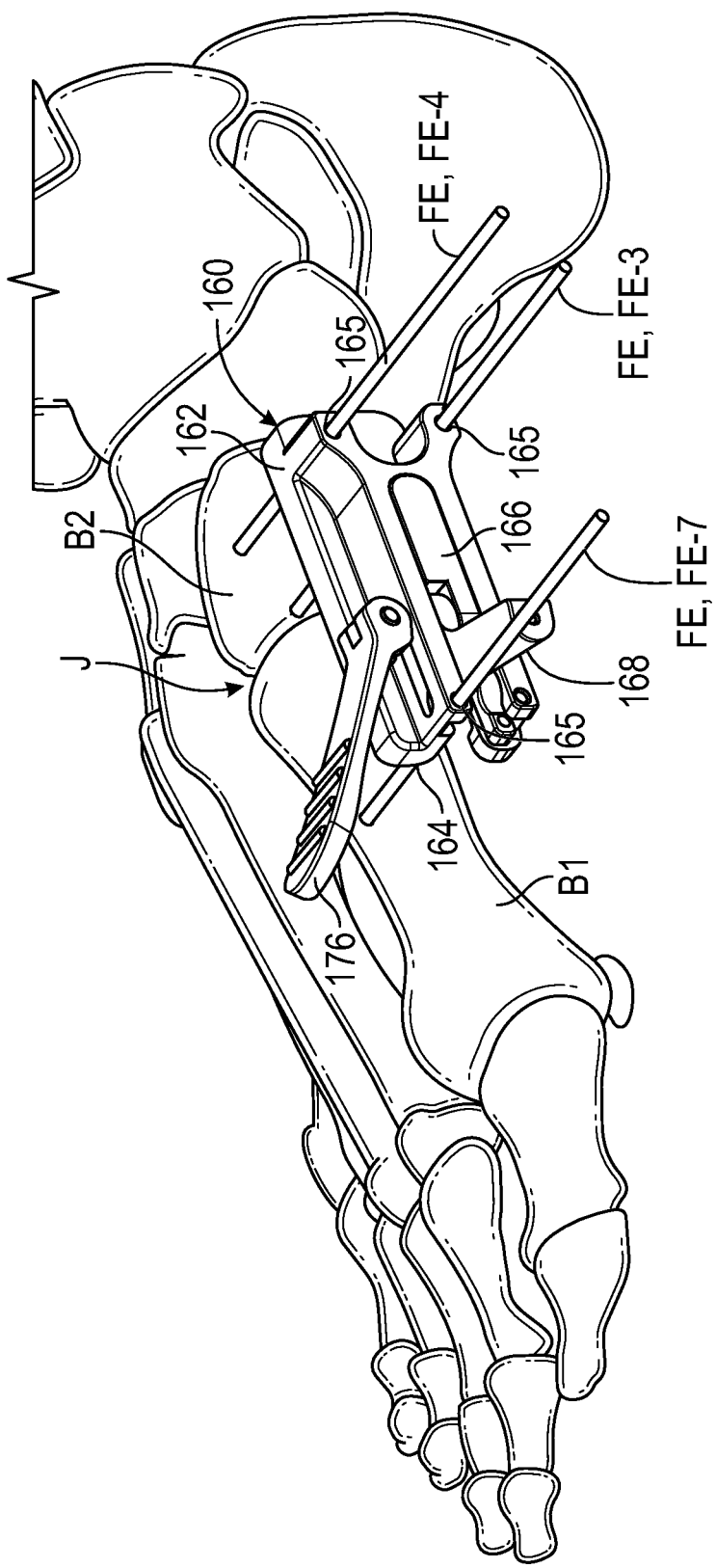
FIG. 21 illustrates placement of another guide assembly along the fixation elements of FIG. 20 and compression of the joint.

The first set of fixation passages 36 of the first guide assembly 20 and the second set of fixation passages 65 of the second guide assembly 60 may be dimensioned to receive a common set of fixation elements, which may be insertable in bone (see, e.g., FIGS. 19 and 21). The first set of fixation passages 36 may be arranged in a first spatial relationship. The second set of fixation passages 65 may be arranged in a second spatial relationship. The first and second spatial relationships can be established by the positions and/or orientations of the respective fixation passages 36, 65 relative to a common coordinate system. In implementations, the first and second spatial relationships are established with respect to openings of the fixation passages 36, 65 along a bone facing side of the respective housing 22, 62, such as along the respective engagement faces 30, 64. The second spatial relationship of the second set of fixation passages 65 may substantially correspond to the first spatial relationship of the first set of fixation passages 36 such that the first and second fixation passages 36, 65 may receive a common set of fixation elements insertable in the bone.

Figure 8:
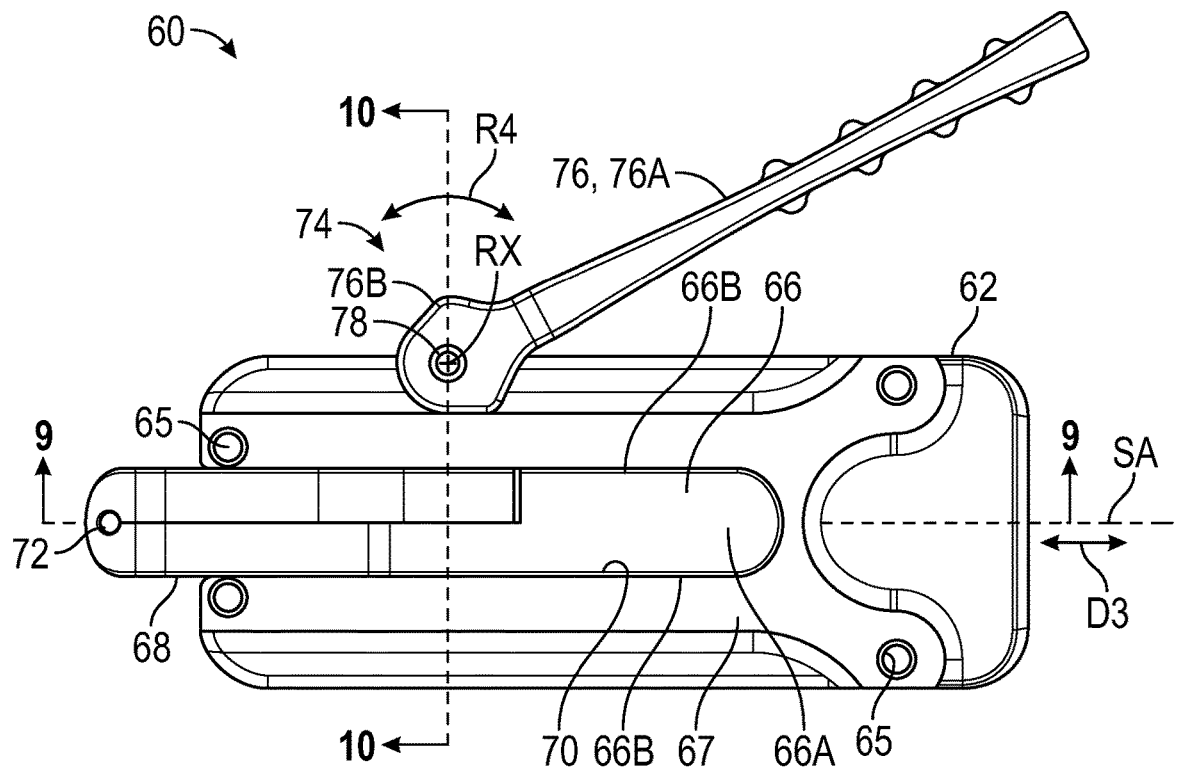
FIG. 8 illustrates a side view of the guide assembly of FIG. 6.
Figure 9:
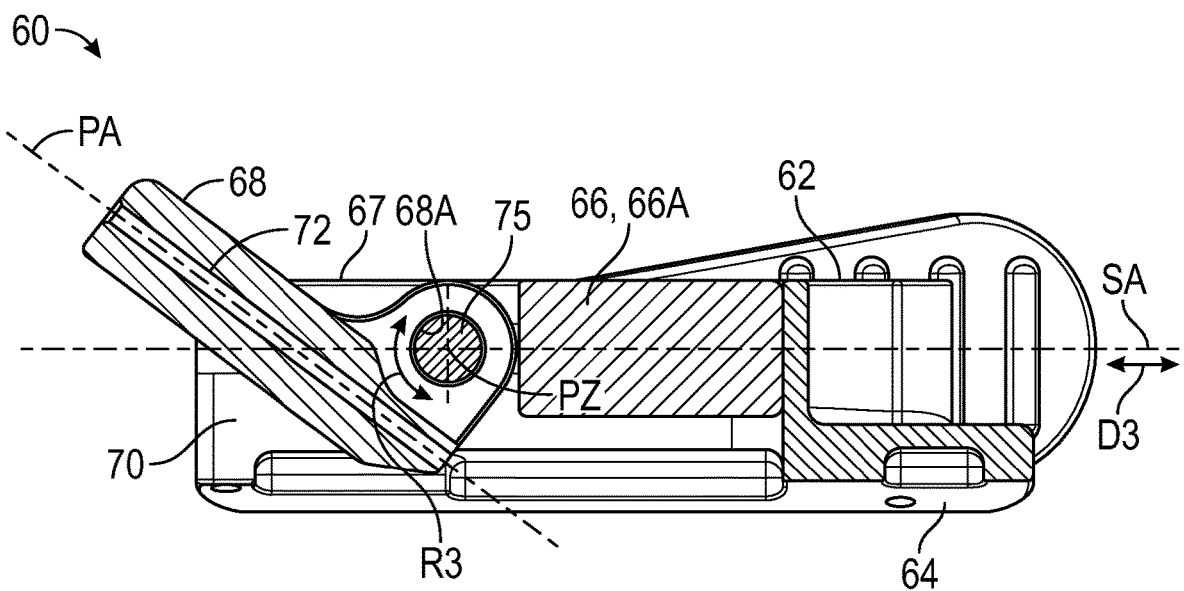
FIG. 9 illustrates a sectional view of the guide assembly taken along line 9-9 of FIG. 8.

The housing 62 may include a first slot 70. The first slot 70 may be dimensioned to extend along a slot axis SA (FIGS. 8 and 9). The first slot 70 may be dimensioned to extend between the engagement face 64 and a second face 67 on opposite sides of the housing 62 (FIGS. 8-10) such that the housing 62 may have a generally elongated, C-shaped geometry.

The guide assembly 60 may include a carrier 66 and a (e.g., second) guide sleeve 68 coupled to the housing 62. The carrier 66 and the guide sleeve 68 may be at least partially captured in a first slot 70 of the housing 62. The guide sleeve 68 may be pivotably coupled or otherwise secured to the carrier 66. The carrier 66 may be dimensioned to extend outwardly from the first slot 70 in an installed position. The carrier 66 may include side walls 66B on opposite sides of a carrier body 66A (FIG. 8). The side walls 66B may be dimensioned to abut walls of the housing 62 to limit rotation of the carrier 66 about the slot axis SA. In implementations, a height of the carrier body 66A between the side walls 66B is substantially equal to a height of the first slot 70 (see, e.g., FIG. 8). The carrier 66 may have an elongated ridge 66R extending along one of the side walls 66B (FIG. 11). The ridge 66R may be captured in a groove 63 along a wall of the first slot 70 (see, e.g., FIGS. 7 and 10).

The guide sleeve 68 may be carried by the carrier 66. The carrier 66 may be translatable in a third direction D3 (FIGS. 8-9) along the slot axis SA to set an axial position of the guide sleeve 68 relative to the slot axis SA.

Referring to FIG. 9, with continuing reference to FIGS. 6-8, the guide sleeve 68 may include at least one (e.g., second) guide passage 72. The guide passage 72 may be dimensioned to receive an instrument, including any of the instruments disclosed herein such as a guide element for positioning a fastener in bone. The guide element may include any of the fixation and guide elements disclosed herein, such as a k-wire or pin. The guide element may be insertable in bone (see, e.g., FIG. 24). In implementations, the guide passage 72 may be dimensioned to receive a cutting instrument for removing tissue. The guide passage 72 may extend along a passage axis PA. The passage axis PA may extend through the first slot 70. The guide sleeve 68 may be pivotable in a third rotational direction R3 relative to the carrier 66 to establish an angle of the passage axis PA relative to the slot axis SA.

Figure 10:
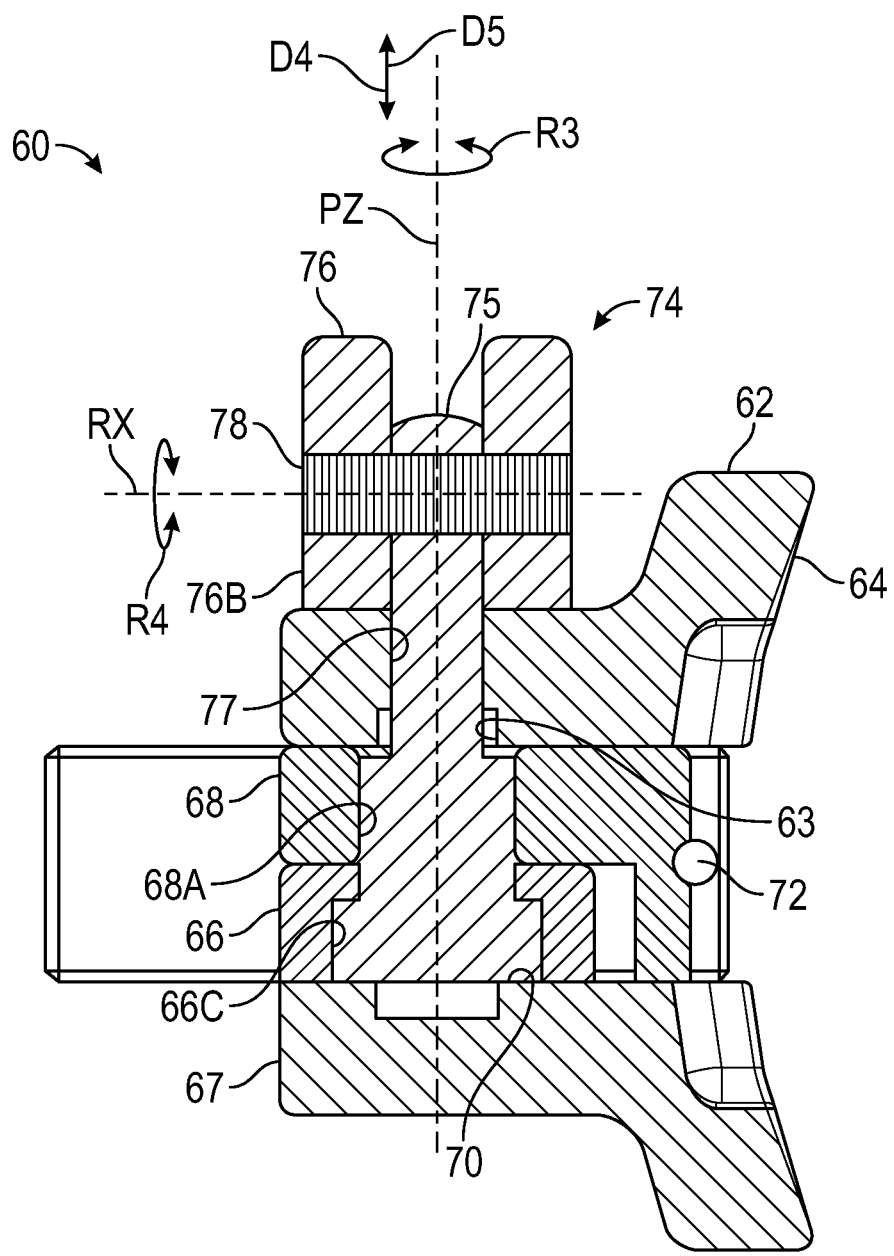
FIG. 10 illustrates a sectional view of the guide assembly taken along line 10-10 of FIG. 8.
Figure 11:
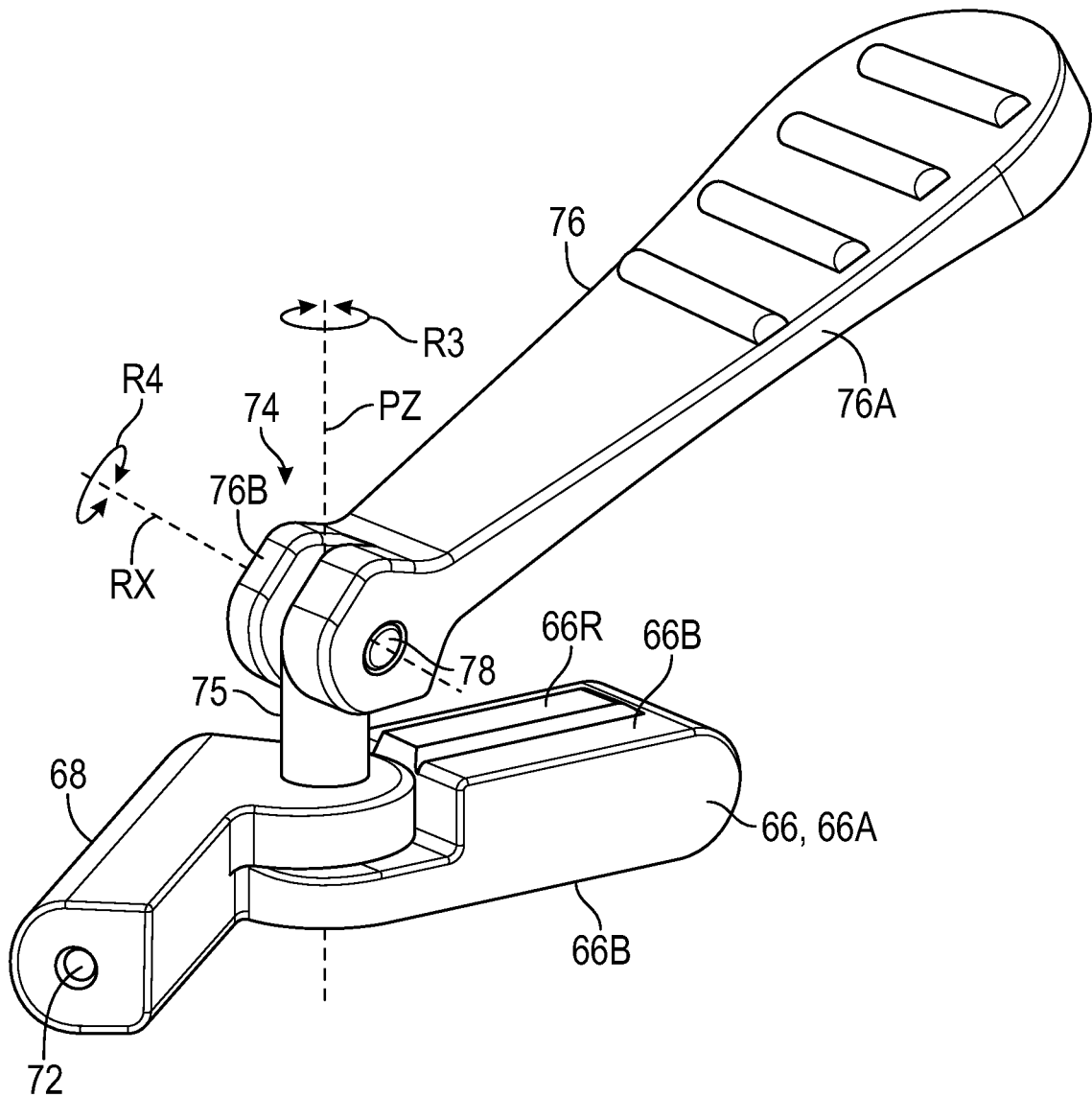
FIG. 11 illustrates a perspective view of the guide assembly of FIG. 6 with a housing of the guide assembly omitted.

Referring to FIGS. 10-11, with continuing reference to FIGS. 8-9, the guide assembly 60 may include a lock mechanism 74 for fixing a position and/or orientation of the guide sleeve 68 relative to the housing 62. The lock mechanism 74 may include a pivot element (e.g., pin) 75 and a locking arm 76. The locking arm 76 may be secured to the pivot pin 75. The guide sleeve 68 may be pivotably coupled to the carrier 66 at the pivot pin 75. The pivot pin 75 may be received in a first bore 66C of the carrier 66 and a second bore 68A of the guide sleeve 68 (FIG. 10). The pivot pin 75 may extend through a third bore 77 of the housing 62 (see also FIGS. 6-7) to fix a position of the guide pin 75 relative to the housing 62. The pivot pin 75 may extend along a pivot axis PZ. The bores 66C, 68A, 77 may be substantially aligned along the pivot axis PZ. In implementations, the third bore 77 may be an elongated slot established in the housing 62. The third bore 77 may extend outwardly from the first slot 70 (see, e.g., FIG. 10). The pivot pin 75 may be translatable along the third bore 77 in the direction D3 (see, e.g., FIG. 9) to set a position of the carrier 66 relative to the slot axis SA.

The guide sleeve 68 may be pivotable in the rotational direction R3 about the pivot axis PZ of the pivot pin 75 (see also FIG. 9). The locking arm 76 may be fixedly attached to the pivot pin 75 with a retention element (e.g., pin) 78. The retention pin 78 may extend along a retention axis RX (FIG. 10). The locking arm 76 may be rotatable in a rotational direction R4 about the retention axis RX between a locked position and an unlocked position.

The locking arm 76 may include an elongated main body 76A and a cam portion 76B. The cam portion 76B may be pivotably coupled to the pivot pin 75 by the retention pin 78. The cam portion 76B may be rotatable to cause the pivot pin 75 and the carrier 66 to translate along the pivot axis PZ. The cam portion 76B may be rotatable between the unlocked position and locked position to move the pivot pin 75 in a fourth direction D4 and/or a fifth direction D5 relative to the pivot axis PZ (FIG. 10). Moving the pivot pin 75 in the fourth direction D4 may establish the unlocked position, and moving the pivot pin 75 in the fifth direction D5 may establish the locked position, or vice versa. Rotating the cam portion 76B in the rotational direction R4 between the unlocked position and the locked position may cause the pivot pin 75 to translate or otherwise move along the pivot axis PZ such that the guide sleeve 68 binds against the housing 62 to limit or otherwise oppose relative movement.

The disclosure herein includes methods of performing an orthopedic procedure. A method may be utilized to perform an arthroplasty for repairing bone deformities or otherwise treating any of the bones and joints disclosed herein, such as one or more bones of the foot, ankle, shoulder, knee, hip or other joints. A method may be utilized to fuse or otherwise fix adjacent bones establishing a joint. In implementations, the method may be used in a Lapidus procedure to treat a bunion deformity, which may include fusing the tarsometatarsal (TMT) joint between the first metatarsal bone and the medial cuneiform. In implementations, the method may be utilized to perform an osteotomy along a bone at a position spaced apart from a joint. The method may be utilized with any of the assemblies, systems and instrumentation disclosed herein, including the first guide assembly 20 and/or second guide assembly 60. Fewer or additional steps than are recited below could be performed within the scope of this disclosure, and the recited order of steps is not intended to limit this disclosure.

Reference is made to a first guide assembly 120 and a second guide assembly 160. The guide assemblies 120, 160 can incorporate any of the features of the guide assemblies 20, 60 disclosed herein. It should be understood that the guide assemblies 120, 160 may be used independent and/or in combination with each other to achieve any of the respective steps of the method 190. In implementations, the first guide assembly 120 may serve as a cutting guide, and the second guide assembly 160 may serve as a targeting guide. The guide assemblies 120, 160 may be positioned externally to facilitate a minimally invasive surgical procedure.

Figure 12:
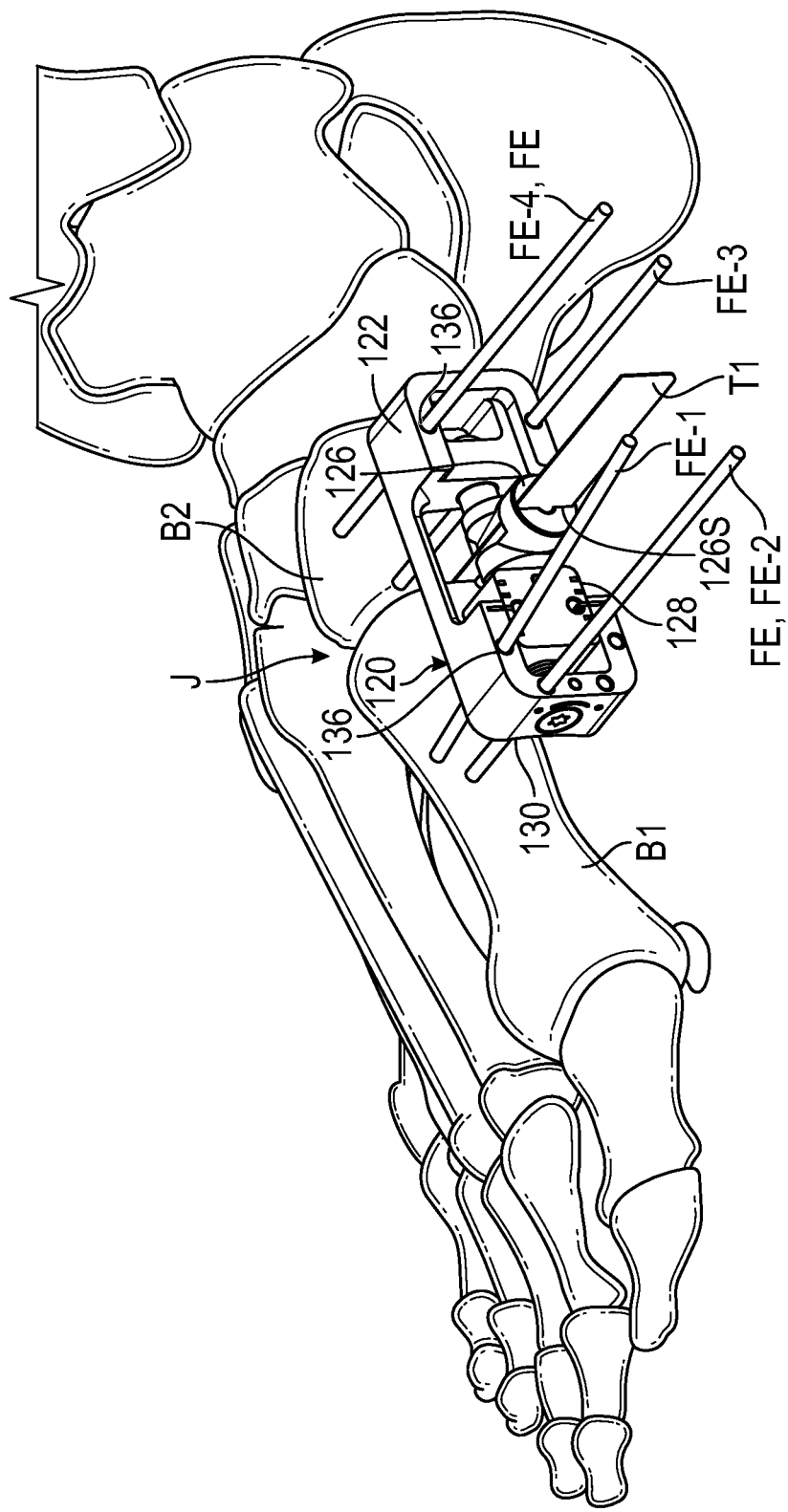
FIG. 12 illustrates a guide assembly and an alignment instrument positioned through a guide sleeve of the guide and into a joint.

Referring to FIG. 12, the first guide assembly 120 may be positioned relative to a joint J. The joint J may be established by opposed articular surfaces of a first bone B1 and second bone B2. In implementations, the joint J may be a tarsometatarsal (TMT) joint. The first bone B1 may be a first metatarsal bone, and the second bone B2 may be the medial cuneiform, or vice versa.

A method may include positioning an engagement face 130 of a first housing 122 of the guide assembly 120 in contact with tissue adjacent to the first and second bones B1, B2. The housing 122 may be positioned to span across the joint J such that the engagement face 130 contacts tissue adjacent to both the first and second bones B1, B2.

Positioning the guide assembly 120 may include positioning a first (e.g., alignment) instrument T1 relative to the joint J. A method may include moving the first instrument T1 through an incision in the skin of the patient. The housing 122 of the guide assembly 120 may be positioned in contact with skin or other tissue adjacent to the incision. The incision may be relatively small, which may facilitate a minimally invasive procedure and healing of the patient. The first instrument T1 may be an alignment tool having a substantially planar geometry. A method may include inserting the instrument T1 through the guide slot 126S of the guide assembly 120, through the incision and then into the joint J. Positioning the instrument T1 may include engaging one or more surfaces of the bones B1, B2 along the joint J. A position and/or orientation of the housing 122 relative to the bones B1, B2 and/or joint J may be set in response to positioning the instrument T1 along the joint J. The guide slot 126S may extend along a guide (e.g. cutting) plane $REF_G$ (see, e.g., FIGS. 15A-15C; see also FIGS. 3-4). The instrument T1 may be positioned along the guide plane $REF_G$ and along the joint J to establish a position of the housing 122 relative to the first and second bones B1, B2.

The position and/or orientation of the housing 122 may be fixed relative to the bones B1, B2 and/or joint J. Various techniques may be utilized, which may include inserting one or more fixation elements FE through respective fixation passages 136 of the housing 122 and then into the first bone B1 and/or second bone B2 to secure the guide assembly 120 to the bones B1, B2. The fixation elements FE may include a first set of fixation elements FE-1 to FE-4. Fewer or more than four fixation elements FE may be utilized to secure the housing 122 to the first and/or second bones B1, B2.

Figure 13:
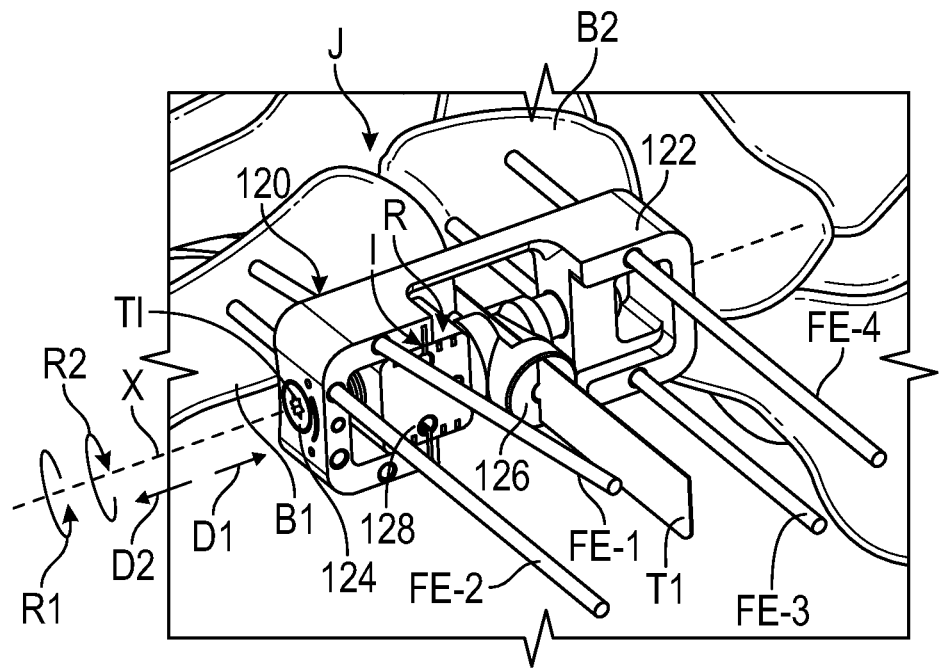
FIG. 13 illustrates the guide assembly of FIG. 12 positioned relative to adjacent bones of the joint.

Referring to FIG. 13, with continuing reference to FIG. 12, a position of a (e.g., first) guide sleeve 126 of the guide assembly 120 may be set relative to the housing 122. Inserting the alignment tool T1 through the guide slot 126S and into the joint J may occur prior to, concurrently and/or subsequent to translating or otherwise setting a position of the first guide sleeve 126. The position of the guide sleeve 126 may be set utilizing any of the techniques disclosed herein. A method may include translating the guide sleeve 126 along a shaft axis X of the drive shaft 124 in response to rotation of the drive shaft 124 in a rotational direction about the shaft axis X. The guide sleeve 126 may be translatable in a first direction D1 along the shaft axis X in response to rotation of the drive shaft 124 in a first rotational direction R1. The guide sleeve 126 may be translatable in a second direction D2 along the shaft axis X in response to rotation of the drive shaft 124 in a second rotational direction R2, which may oppose the first rotational direction R1. The first rotational direction R1 may oppose the second rotational direction R2. A tool may be utilized to engage an interface TI along the drive shaft 124 to rotate the drive shaft 124 about the shaft axis X.

The position of the guide block 128 and/or guide sleeve 126 may set relative to the drive axis X. The guide assembly 120 may include indicia for setting the position of the guide block 128 and/or guide sleeve 126. The indicia may include a ruler R and an indicator I adjacent to the ruler R (see also FIGS. 1 and 3). A method may include aligning the indicator I with a selected position along the ruler R to establish a specified position of the guide sleeve 126 and/or guide block 128 relative to the drive axis X. The selected position may substantially correspond to a predetermined value. The predetermined value may be determined inter-operatively or may be determined pre-operatively and may be specified in a pre-operative plan.

Figure 14:
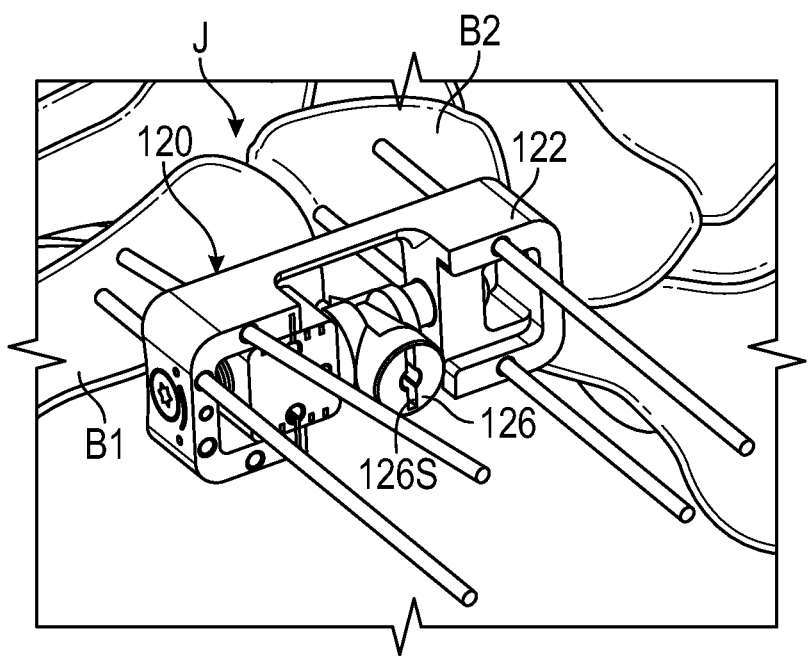
FIG. 14 illustrates removal of the alignment instrument from the guide assembly of FIG. 13.

Referring to FIG. 14, the instrument T1 may be removed from the joint J and the guide slot 126S. Removing the instrument T1 may occur subsequent to fixing the position of the housing 122 relative to the bones B1, B2 and/or joint.

Figure 15A:
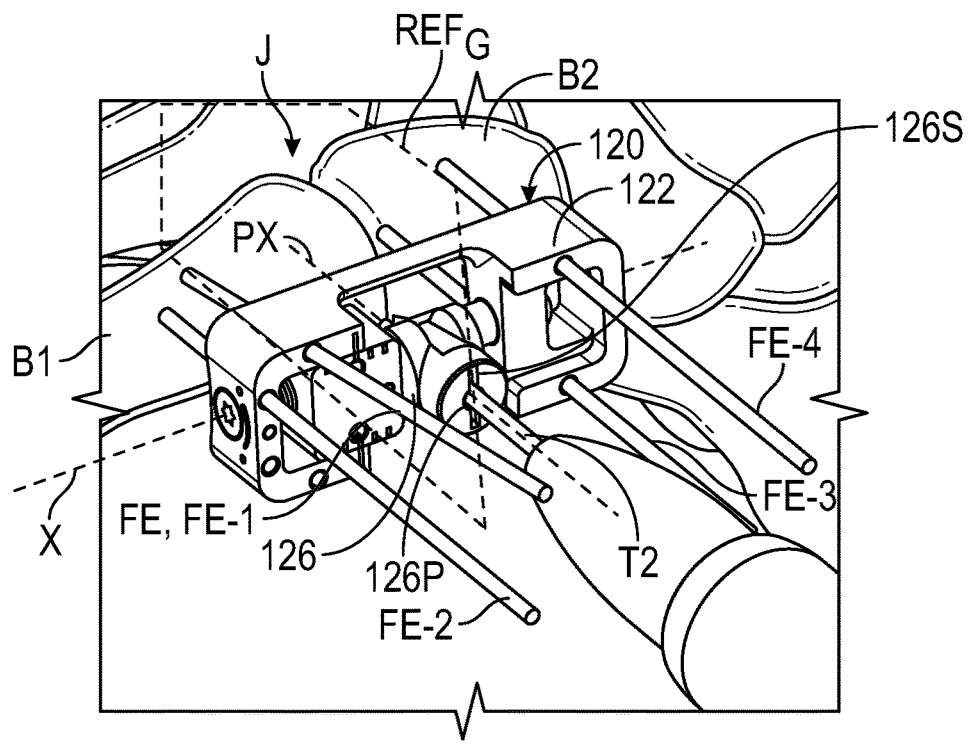
FIG. 15A illustrates a cutting instrument positioned through the guide sleeve of the guide assembly of FIG. 14 at a first position and removal of tissue along the joint.

Referring to FIG. 15A, with continuing reference to FIGS. 13-14, a method may include positioning a second (e.g., cutting) instrument T2 relative to the bones B1, B2 and/or joint J. The instrument T2 may be a cutting instrument adapted to remove a portion of bone or other tissue, such as cartilage, cortical bone and/or cancellous bone from articular surface(s) of the joint J and/or other portions of the bones B1, B2, including non-articular surface(s) of the bones B1 and/or B2 spaced apart from the joint J. The instrument T2 can include any of the instruments disclosed herein, such as a rotatory cutting tool (e.g., burr) or other cutting instrument adapted to remove bone or other tissue, including any of the instruments disclosed herein.

A method may include inserting the instrument T2 through the first guide passage 126P and/or slots 126S and through the incision adjacent the joint J. The instrument T2 may be substantially aligned with the guide plane $REF_G$. A position and/or orientation of the guide plane $REF_G$ may be established according to a respective resection plane. The resection plane may be determined inter-operative or pre-operatively. A predetermined value along the ruler R may substantially correspond to the resection plane. Aligning the indicator I relative to the ruler R may establish a position of the guide plane $REF_G$ and instrument T2 relative the bones B1, B2 and/or joint J (FIG. 14).

Tissue may be removed from at least one of the first and second bones B1, B2 along the joint J and/or other portions of the bones B1, B2. A method may include sweeping the instrument T2 in an arc path along the guide plane $REF_G$ to remove tissue from the joint J and/or other portions of the first and/or second bones B1, B2, which may occur in a response to pivoting the first guide sleeve 126 about the shaft axis X. A method may include sweeping the instrument T2 in an arc path at least 10 degrees, or more narrowly at least 45 degrees but no more than 180 degrees, about the shaft axis X such that the instrument T2 intersects and engages a thickness of the respective bone(s) B1, B2. Each arc path may intersect the first bone B1 and/or second bone B2 to remove a portion of tissue with the instrument T2. The guide plane $REF_G$ may intersect both, or only one of, the bones B1, B2 at the set position of the guide sleeve 126. In implementations, sweeping the instrument T2 in the arc path along the guide plane $REF_G$ may cause removal of tissue from the second bone B2, but not the first bone B1.

Figure 15B:
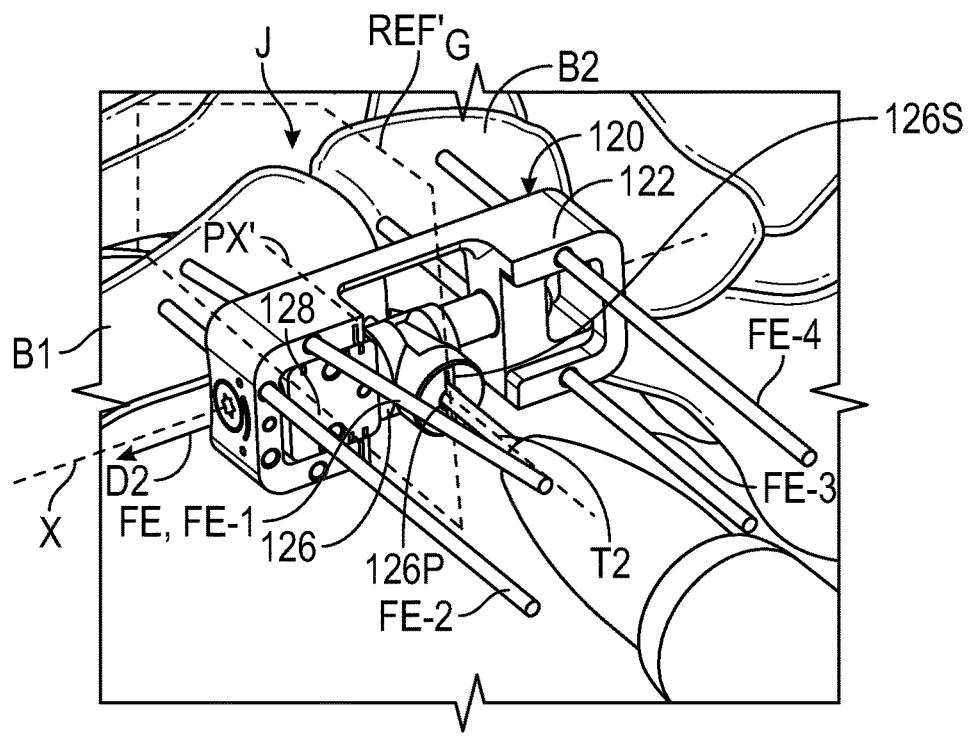
FIG. 15B illustrates the cutting instrument positioned through the guide sleeve of the guide assembly of FIG. 14 at a second position and removal of tissue along the joint.

Method steps may be repeated to remove tissue from other portions of the bones B1, B2 and/or joint J. Referring to FIG. 15B, with continuing reference to FIG. 15A, a method may include moving the guide sleeve 126 and/or guide block 128 from a first position (e.g., FIG. 15A) to a second, different position (e.g., FIG. 15B) relative to the drive axis X, which may be associated with another determined value of the ruler R (FIG. 13). A method may include repeating the removal of instrument T2 from the joint J and the guide passage 126P, and then translating the guide sleeve 126 and/or guide block 128 in the direction D1 and/or direction D2 to establish another position of the guide plane $REF_G'$ relative to the drive shaft X and/or relative to the bones B1, B2 and joint J. Situating the guide sleeve 126 at the second position to remove tissue from bone B1 and/or bone B2 may occur subsequent to situating the guide sleeve 126 at the first position, or vice versa. In implementations, the first position of the guide plane $REF_G$ may be associated with removal of tissue from the second bone B2 (e.g., FIG. 15A), and the second position of the guide plane $REF_G'$ may be associated with removal of tissue from the first bone B1 (e.g., FIG. 15B), or vice versa. The guide plane $REF_G'$ may be established at a position relatively more proximal or distal of the guide plane $REF_G$.

Figure 15C:
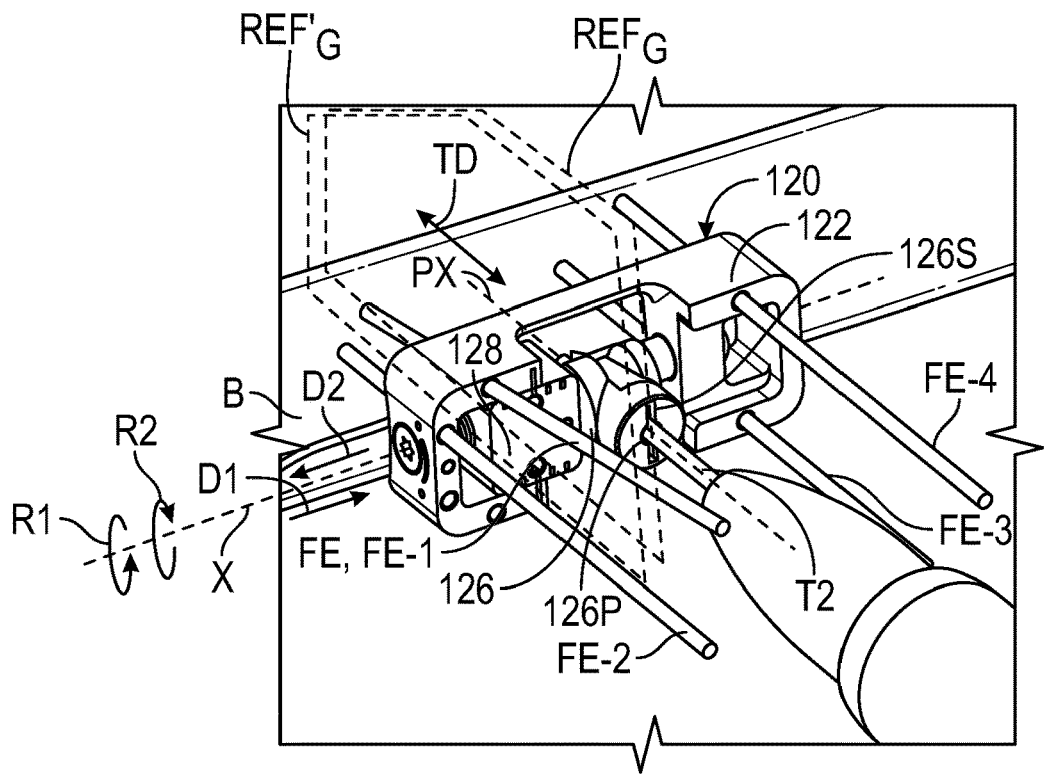
FIG. 15C illustrates the cutting instrument positioned through the guide sleeve of the guide assembly of FIG. 14 and removal of bone.

In implementations, methods may include positioning the guide assembly 120 to perform an osteotomy, as illustrated in FIG. 15C. The guide assembly 120 may be positioned relative to a bone B. The bone B may be any of the bones disclosed herein, such as a metatarsal, cuneiform or calcaneus bone of the foot, or another bone such as a tibia or femur. The shaft axis X of the guide assembly 120 may be generally parallel to a longitudinal axis of the bone B. A guide plane $REF_G$ may be established by the guide assembly 120 to resect or otherwise remove a portion of the bone B. The guide plane $REF_G$ may be set such that the resection is established at a position spaced apart from a joint to establish an osteotomy. A method of performing the osteotomy may include sweeping or otherwise moving the instrument T2 along the guide plane $REF_G$ to resect or otherwise remove a portion of the bone B. Methods may include translating the guide sleeve 126 and/or guide block 128 in a direction D1 and/or direction D2 to establish another position of the guide plane $REF_G'$ relative to the drive shaft X and/or relative to the bone B and then resecting or otherwise removing another portion of the bone B along the guide plane $REF_G'$. The guide planes $REF_G$, $REF_G'$ may be substantially parallel to each other. A method may include moving a position of the housing 122 such that the guide planes $REF_G$, $REF_G'$ intersect or are otherwise transverse to each other. A transverse arrangement of the guide planes $REF_G$, $REF_G'$ may be utilized to establish a wedge osteotomy. The instrument T2 may be moved in a direction TD relative to the passage axis PX to adjust or otherwise set a (e.g., cutting) depth of the instrument T2. The cutting depth may be less than, equal to, or greater than a thickness of the bone B along the guide plane $REF_G$.

Figure 16A:
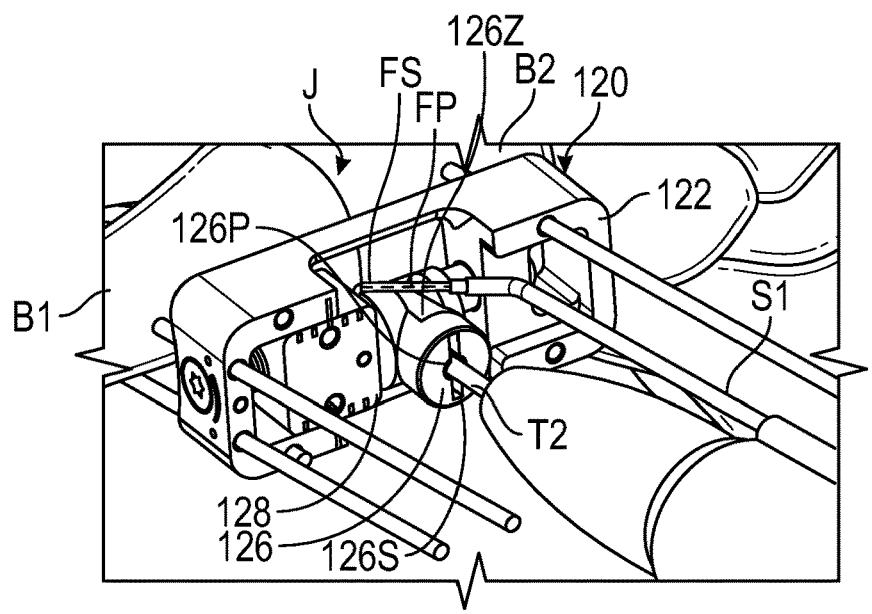
FIGS. 16A-16B illustrate an irrigation system positioned relative to the cutting instrument and guide assembly of FIG. 15A.
Figure 16B:
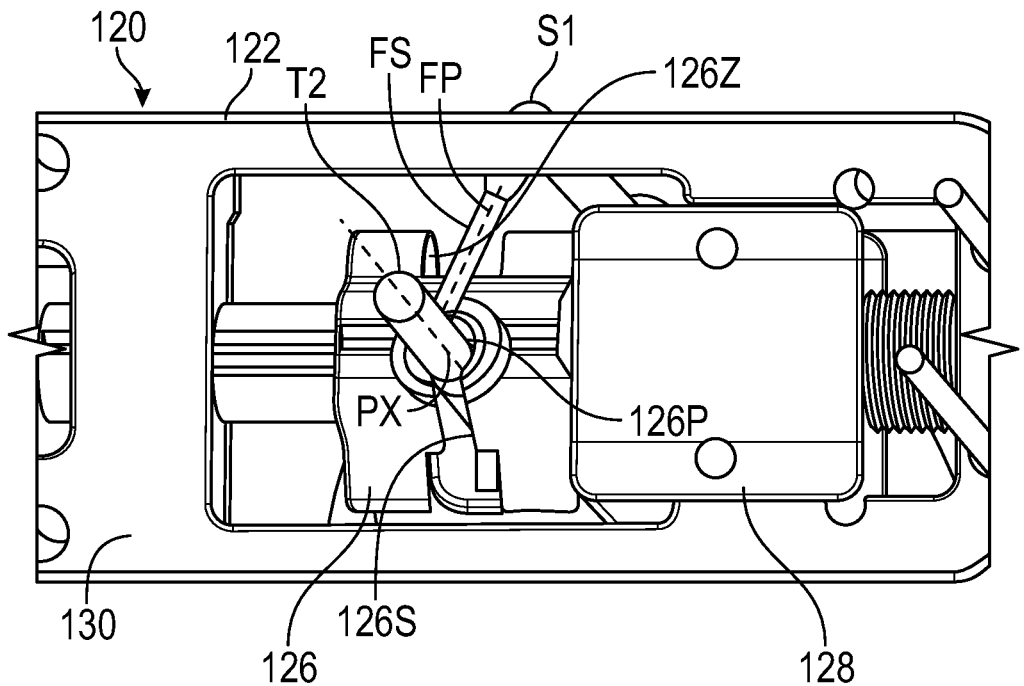

Referring to FIGS. 16A-16B, with continuing reference to FIGS. 15A-15B, a method may include irrigating the surgical site during removal of tissue from the first and/or second bones B1, B2. The guide assembly 120 may be adapted to cooperate with an irrigation system S1. The irrigation system S1 may be situated adjacent to the guide sleeve 126. The irrigation system S1 may be configured to communicate a pressurized fluid (e.g., water) stream FS along a fluid path FP to irrigate the surgical site. The fluid path FP may be established in a direction from the irrigation system S1 towards the instrument T2. The fluid path FP may extend along the guide plane $REF_G$ (e.g., guide planes $REF_G$ and/or $REF_G'$ of FIGS. 15A-15B). The fluid path FP may be established along a passageway between the housing 122 and the guide sleeve 126. The guide sleeve 126 may include a second (e.g., access) slot 126Z dimensioned to establish a through passage for the fluid path FP. The fluid path FP may extend through the slot 126Z such that the fluid stream FS is substantially unobstructed by the guide system 120 during irrigation. The fluid stream FS may impinge on the instrument T2 to provide cooling augmentation to the instrument T2. A projection of the fluid path FP may intersect a projection of the passage axis PX of the guide passage 126P (FIG. 16B). The passageway established by the guide assembly 120 may facilitate irrigation of the surgical site with a relatively compact arrangement.

Figure 17:
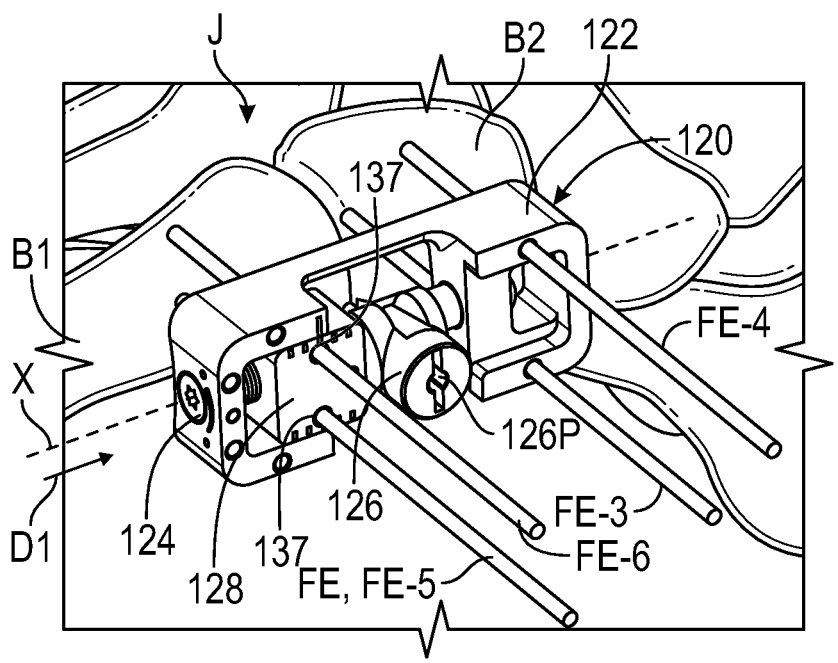
FIG. 17 illustrates removal of the cutting instrument from the guide sleeve of FIG. 15A, placement of fixation elements through a guide block of the guide assembly and compression of the joint.

Referring to FIG. 17, with continuing reference to FIG. 15A-15B, the instrument T2 may be removed from the first guide passage 126P of the guide sleeve 126. One or more of the fixation elements FE may be removed from the housing 122, such as the first and second fixation elements FE-1, FE-2 (FIG. 15A-15B). The joint J may be compressed. One or more resected or otherwise altered surfaces of the bone B1 and/or bone B2 may contact opposing surfaces of the adjacent bone B2/B1 of the compressed joint J.

Various techniques may be utilized to compress the joint J, which may include positioning one or more fixation elements through respective block passages 137 of the guide block 128 and then into the bone B1. The fixation elements FE may include fifth and sixth fixation elements FE-5, FE-6 inserted or otherwise positioned through the respective block passages 137 and then into the first bone B1. A method may include removing one or more fixation elements FE from the housing 122, such as the fixation elements 1-E-1, FE-2 (FIG. 16). The guide block 128 may be movable relative to the drive axis X and housing 122, which may occur subsequent to removing the fixation elements FE-1, FE-2 from the bone B1.

Setting a position of the guide block 128 relative to the housing 122 and bones B1, B2 and/or joint J may occur such that the first and second bones B1, B2 may compress against, or otherwise abut, each other to establish a compressed state of the joint J. The guide block 128 may be translated or otherwise moved in the first direction D1 along the shaft axis X to reduce a distance between the fixation elements 1-B-3, FB-4 on one side of the joint J and the fixation elements FE-5, FE-6 on another side of the joint J. In implementations, the shaft axis X may be oriented generally in a proximal/distal direction relative to the patient, and the first direction D1 may generally extend proximally relative to the patient.

Rotating the drive shaft 124 to cause fixation elements FE-3, FE-4 and fixation elements FE-5, FE-6 to compress the first and second bones B1, B2, respectively, against each other can establish the compressed state of the joint J. This may occur subsequent to removing tissue from the first bone B1, second bone B2 and/or other portions of the joint J.

Figure 18:
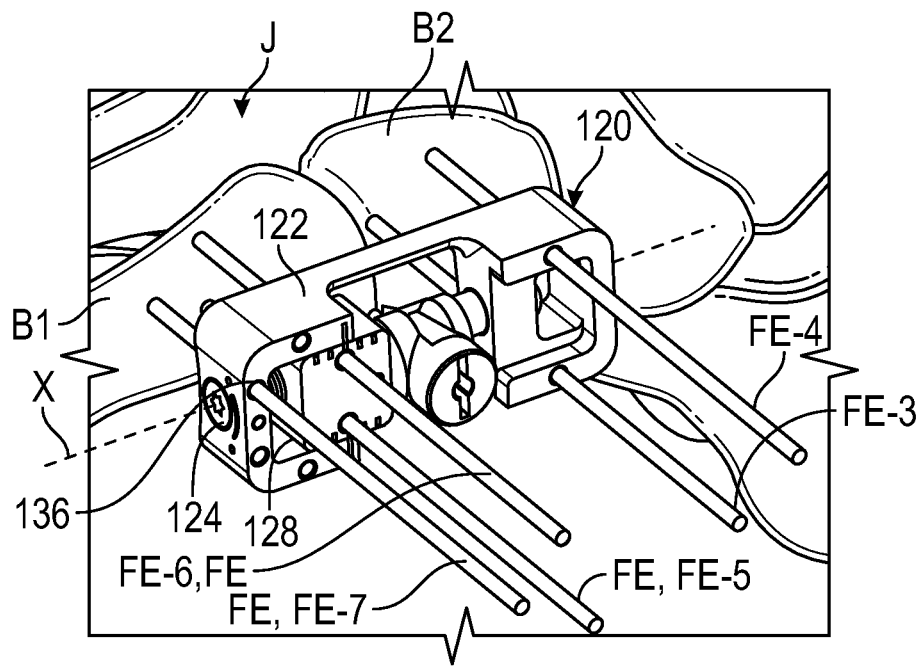
FIG. 18 illustrates placement of fixation elements through a housing of the guide assembly of FIG. 17.

Referring to FIG. 18, with continuing reference to FIG. 17, a position of the first and second bones B1, B2 may be fixed relative to each other in the compressed state of the joint J. One or more fixation elements FE can be positioned through respective fixation passages 136 of the housing 122 and then into the first bone B1 and/or second bone B2 to secure the guide assembly 120 to the bones B1, B2 in the compressed state, such as a seventh fixation element FE-7 into the first bone B1. Fixation element FE-7 can cooperate with the fixation elements FE-3, FE-4 to maintain a distance between the first bone B1 and second bone B2 associated with the compressed state of the joint J.

Referring to FIG. 19, with continuing reference to FIG. 18, one or more fixation elements FE may be removed from the guide block 128, such as the fixation elements FE-5, FE-6 (FIG. 18), which may occur subsequent to establishing the compressed state of the joint J.

Figure 20:
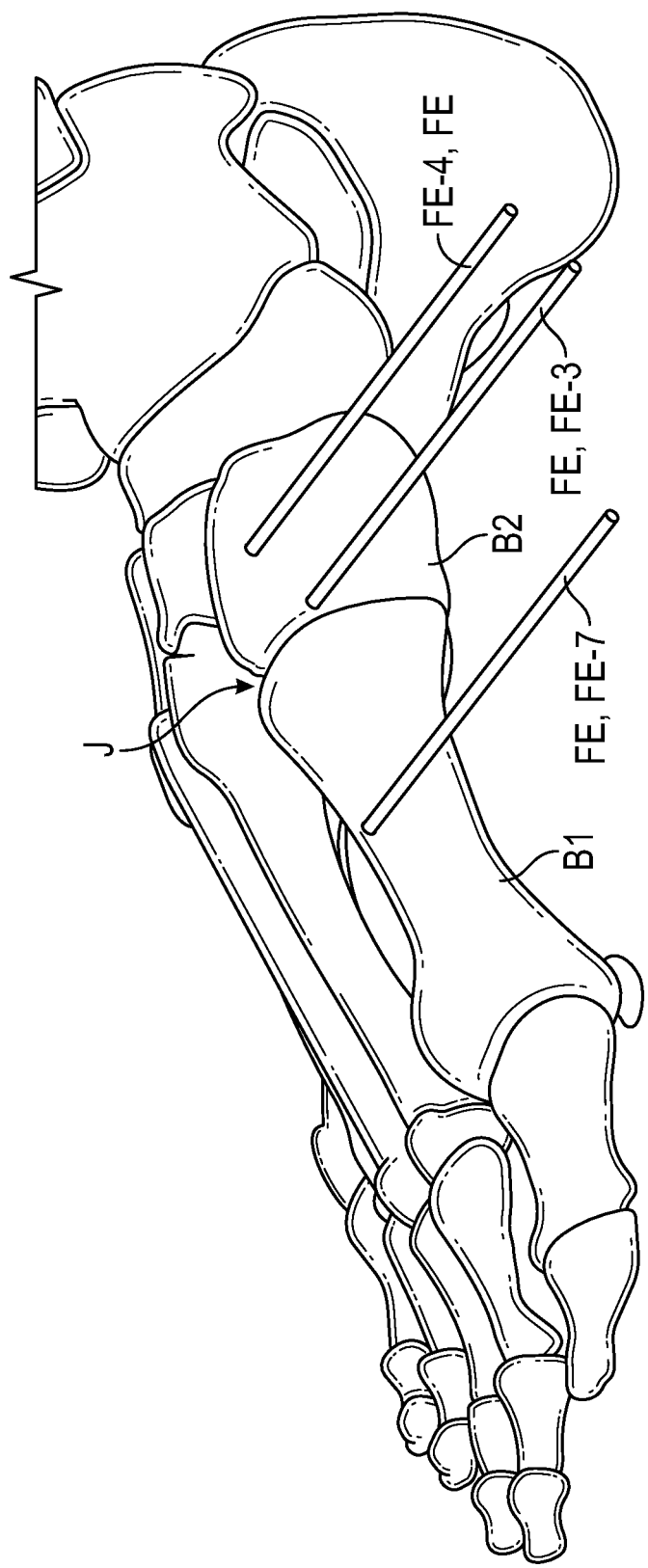
FIG. 20 illustrates removal of the guide assembly from the fixation elements of FIG. 19.

Referring to FIG. 20, with continuing reference to FIG. 19, the guide assembly 120 may be removed from the surgical site. The guide assembly 120 may be removed from the fixation elements FE, such as fixation elements FE-3, FE-4 and FE-7. Fixation elements FE-3, FE-4 and FE-7 may remain in the respective bones B1, B2 subsequent to removing the guide assembly 120. The distance between the fixation elements FE-3, FE-4 and the fixation element FE-7 may be associated with the compressed state of the joint J. The distance between the fixation elements FE-3, FB-4 and the fixation element FE-7 may increase or otherwise vary subsequent to removing the guide 120 from the surgical site such that the joint J may at least partially decompress.

Referring to FIG. 21, with continuing reference to FIG. 20, the second guide assembly 160 may be positioned relative to the first and second bones B1, B2 of the joint J, which may occur subsequent to removing tissue from the first bone B1, second bone B2 and/or other portions of the joint J. An engagement face 164 of a (e.g., second) housing 162 of the guide assembly 160 may be positioned in contact with tissue adjacent to the first and second bones B1, B2. The housing 162 may be positioned to span across the joint J such that the engagement face 164 contacts tissue of the patient adjacent to both the first and second bones B1, B2. In implementations, the engagement face 164 may be dimensioned to follow a contour of skin adjacent to the joint J.

Substantially or completely reestablishing compression of the joint J may occur in response to inserting the fixation elements FE through respective fixation passages 165 of the housing 162 and then into the respective bones B1, B2. The fixation elements FE may include fixation elements FE-3, FE-4 and/or FE-7 positioned by the guide assembly 120. The housing 162 of the guide assembly 160 can slide over the fixation elements FE-3, FE-4 and/or FE-7 and into abutment with the first bone B1 and/or second bone B2, which may compress the bones B1, B2 together or otherwise cause the bones B1, B2 to abut each other. A distance between the bones B1, B2 may be reduced. The set of fixation passages 165 of the housing 162 utilized to reestablish the compressed state of the joint J may be arranged in a spatial relationship that substantially corresponds to a spatial relationship of the set of fixation passages 136 that receive the common set of fixation elements FE, such as the fixation elements FE-3, FE-4 and/or FE-7 (see, e.g., FIGS. 19 and 21). Utilizing a common set of fixation elements FE, such as FE-3, FE-4 and/or FE-7, to position the housing 162 of the guide assembly 160 may substantially establish the same alignment and compression between the bones B1, B2 established by the housing 122 of the guide assembly 120, which may improve mobility and fusion between bones B1, B2.

Figure 22:
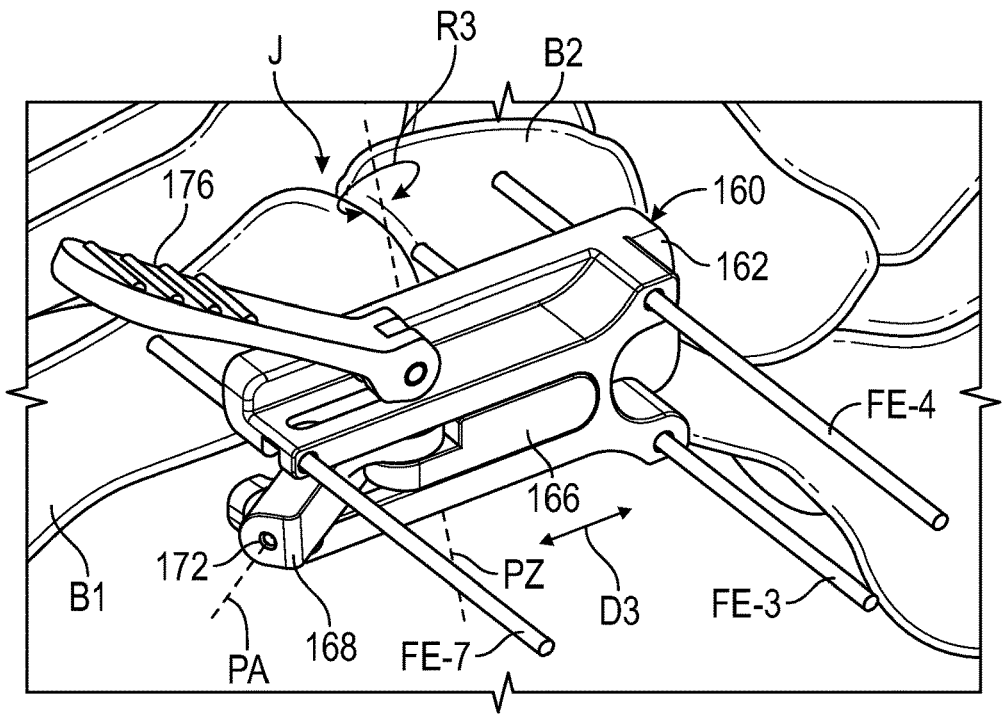
FIG. 22 illustrates positioning a guide sleeve of the guide assembly of FIG. 21.

Referring to FIG. 22, with continuing reference to FIG. 21, a position of a second guide sleeve 168 of the guide assembly 160 may be set relative to the second housing 162. The carrier 166 of the guide assembly 160 can be translated or otherwise moved in a third direction D3 relative to the housing 162. The guide sleeve 168 can be oriented relative to the housing 162. The guide sleeve 168 may be pivoted in a third rotational direction R3 about a pivot axis PZ of a pivot pin 175. Pivoting the guide sleeve 168 may occur such that a passage axis PA of a guide passage 172 of the guide sleeve 168 is set at a predetermined position and/or orientation relative to the first bone B1, second bone B2 and/or joint J (see, e.g., FIGS. 23-24).

Figure 23:
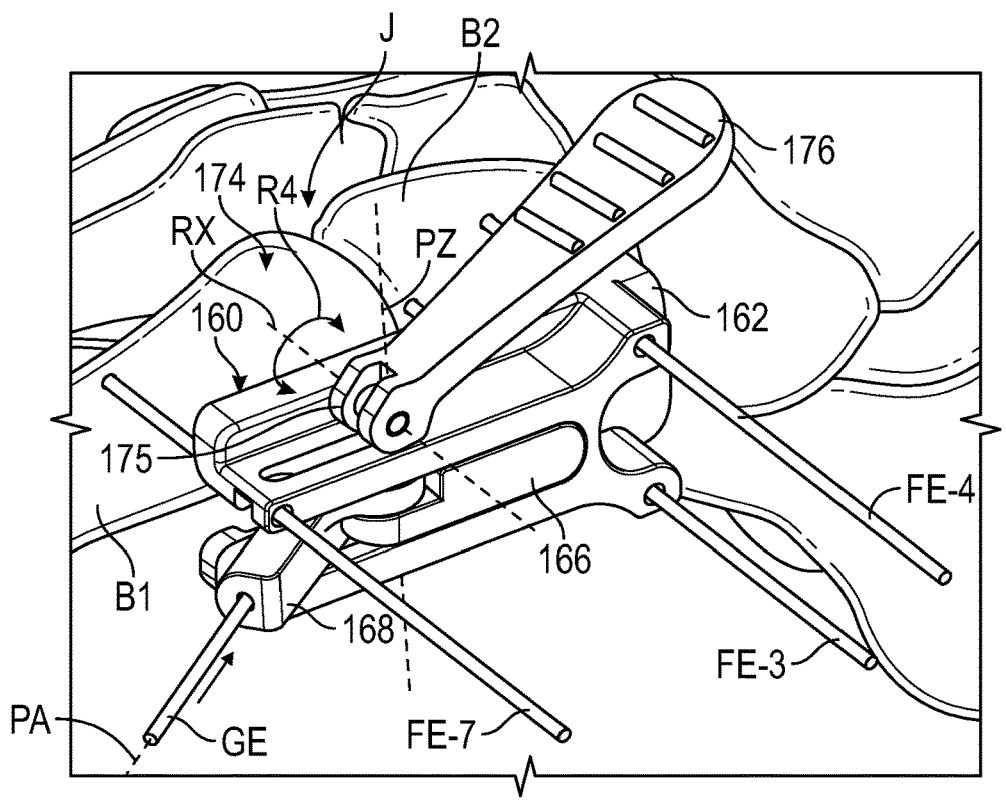
FIG. 23 illustrates actuation of a lock mechanism of the guide assembly of FIG. 22 between an unlocked configuration and a locked configuration.

Referring to FIG. 23, with continuing reference to FIG. 22, a position and/or orientation of the guide passage 172 of the guide sleeve 168 may be set. A lock mechanism 174 of the guide assembly 160 can be actuated, which may include translating the pivot pin 175 along the pivot axis PZ to cause the second guide sleeve 168 to bind against the second housing 162. This may occur in response to rotating a locking arm 176 coupled to the pivot pin 175. Locking arm 176 may rotate in a fourth rotational direction R4 about a retention axis RX between an unlocked position (e.g., FIG. 22) and a locked position (e.g., FIG. 23).

Figure 24:
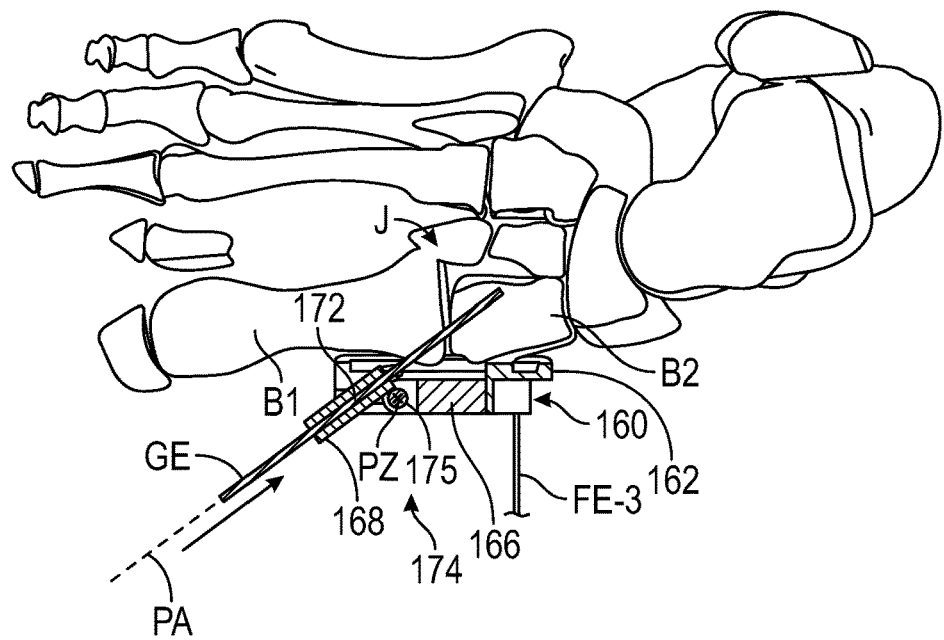
FIG. 24 illustrates a sectional view of the guide element relative to the joint of FIG. 23.

Referring to FIGS. 23-24, one or more guide element GE can be positioned into the first bone B1, second bone B2 and/or across the joint J. The guide element GE may include any of the guide and fixation elements disclosed herein, such as a k-wire or pin. The guide element GE can be inserted into and through the guide passage 172 and along the respective passage axis PA, and then moving the guide element GE across the joint J. The guide element GE may extend through a resection plane associated with the guide plane $REF_G$ established by the guide assembly 120 relative to the joint J (see, e.g., FIG. 16). Inserting the guide element GE across the joint J may occur subsequent to substantially reestablishing a compressed state of the joint J, which may promote fusion between adjacent surfaces of the first bone B1 and second bone B2 that may have been altered by removal of tissue. In implementations, a position and orientation of the guide element GE relative to the joint J may be determined. FIG. 24 may represent an example image of the joint J. The surgeon may reposition the guide element GE relative to the joint J in response to determining a deviation from the surgical plan.

Figure 25:
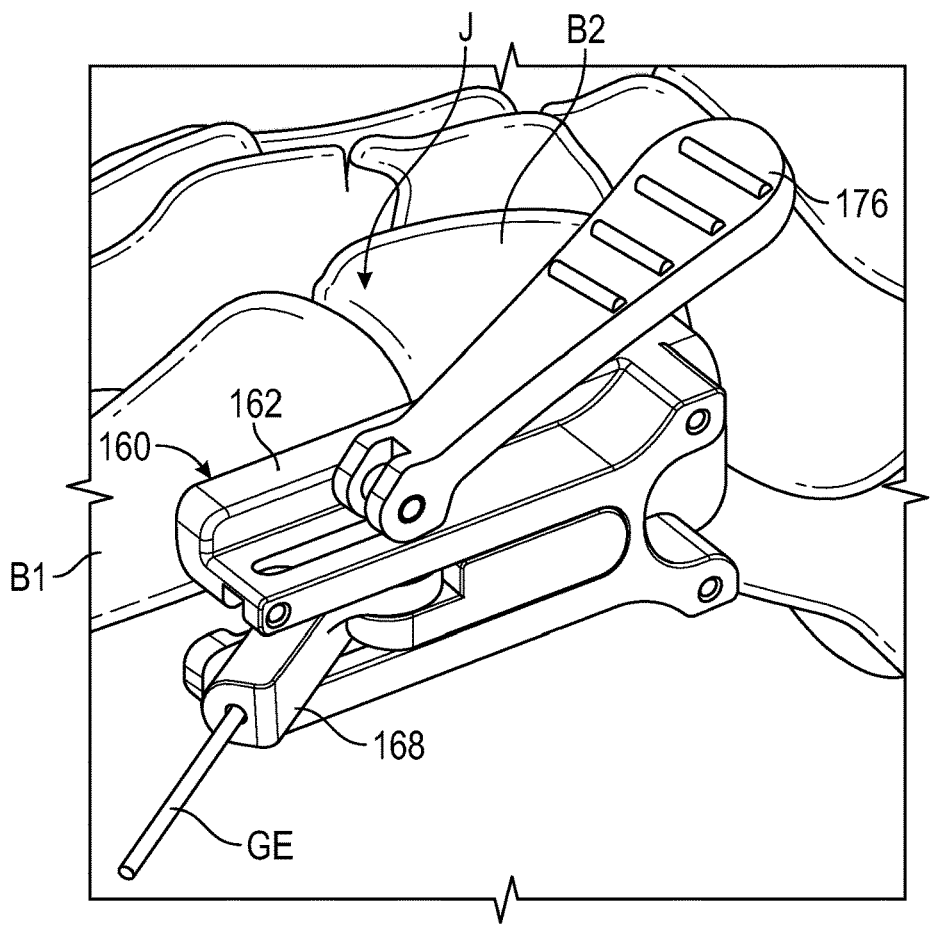
FIG. 25 illustrates a perspective view of the guide assembly of FIG. 23 in the locked configuration.
Figure 26:
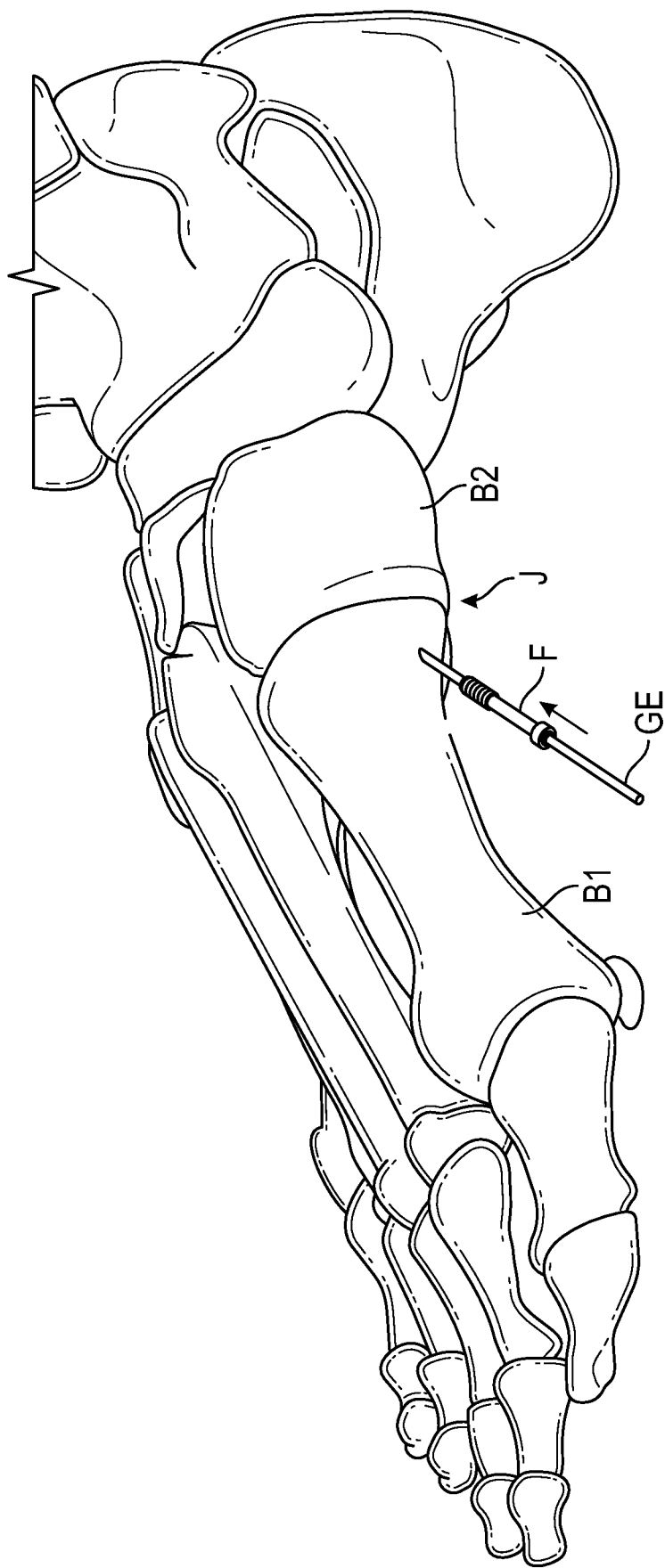
FIG. 26 illustrates a fastener positioned along the guide element relative to the joint of FIG. 25.

Referring to FIGS. 25 and 26, with continuing reference to FIG. 23, the guide assembly 160 may be removed from the surgical site. Fixation elements FE-3, FE-4, FE-7 may be removed from the second housing 162 and from the respective bones B1, B2 (FIG. 25) and then removing the second housing 162 from the surgical site (FIG. 26).

Figure 27:
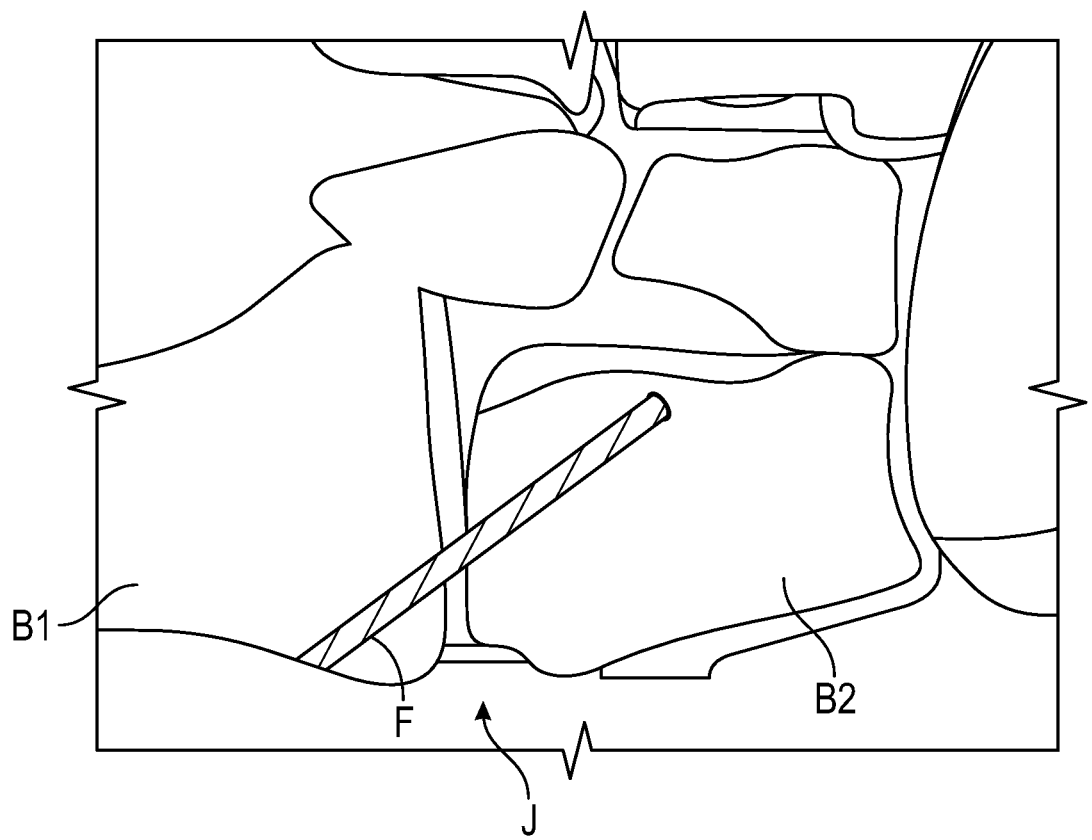
FIG. 27 illustrates the fastener positioned across the joint of FIG. 26.

Referring to FIGS. 26 and 27, the bones B1, B2 may be fixed or otherwise secured together while the bones B1, B2 are in a compressed state, which may promote fusion between surfaces of the bones B1, B2. Various techniques may be utilized to secure the bones B1, B2 together, such as with a bone plate and/or one or more fasteners. In implementations, a fastener F may be moved along the guide element GE into the first bone B1, then across the joint J and into the second bone B2 to fix a position of the first bone B1 and the second bone B2 relative to each other. The fastener F may be a compression screw, nail, etc. One or more finishing operations may be performed, including closing an incision previously made to access the joint J.

The novel devices and methods of this disclosure provide versatility and precision in placing and guiding instruments at a surgical site. The disclosed systems and methods may be utilized for repairing bone deformities, such a Lapidus procedure for correcting a bunion deformity. One or more guides may be utilized to position instruments relative to bones and/or joints. The guides may be utilized for restricting movement of a cutting instrument and/or placing a fixation element to secure adjacent bones that establish a joint. The guides may include a cutting guide having a guide sleeve and/or guide block moveable relative to a drive shaft. The guides may include a trajectory guide for positioning one or more guide elements relative to bones and/or joints. The trajectory guide may include a guide sleeve for orienting a guide element relative to the bones and/or joint. A position of each guide sleeve may be determined interoperatively and/or pre-operatively and may be specified in a preoperative plan. The predetermined positions may be utilized to precisely place and guide a cutting instrument for removing tissue from articular surfaces of the joint and to precisely place fixation element(s) for fixing together the bones, which may improve healing and mobility of the patient. The cutting block may be utilized to compress the joint subsequent to the removal of tissue, which may improve placement of the fixation element(s) and fusion of the joint surfaces. The disclosed guides may be reusable. The disclosed systems and methods may be utilized to reduce operative time and complexity.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should further be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A guide assembly for an orthopaedic procedure comprising:
    a housing dimensioned to contact tissue;
    a drive shaft coupled to the housing, the drive shaft extending along a shaft axis;
    a guide sleeve carried by the drive shaft, the guide sleeve including a guide passage extending along a passage axis, the guide passage dimensioned to receive an instrument, the guide sleeve translatable along the shaft axis in response to rotation of the drive shaft, and the guide sleeve pivotable about the shaft axis to sweep the passage axis along a guide plane; and
    a guide block carried by the drive shaft, the guide block including one or more block passages dimensioned to receive a respective fixation element;
    wherein the guide block and the guide sleeve are translatable as a unit along the shaft axis in response to rotation of the drive shaft, and the guide block includes sidewalls dimensioned to abut walls of the housing to limit rotation of the guide block about the shaft axis.

2. The guide assembly as recited in claim 1, wherein the guide sleeve includes a guide slot extending along the guide plane, and the guide slot is dimensioned to receive an elongated instrument insertable into a joint.

3. The guide assembly as recited in claim 1, wherein the guide sleeve and the guide block are translatable along the shaft axis in response to articulation of a worm drive mechanism.

4. A guide assembly for an orthopaedic procedure comprising:
    a housing dimensioned to contact tissue;
    a drive shaft coupled to the housing, the drive shaft extending along a shaft axis;
    a guide sleeve carried by the drive shaft, the guide sleeve including a guide passage extending along a passage axis, the guide passage dimensioned to receive an instrument, the guide sleeve translatable along the shaft axis in response to rotation of the drive shaft, and the guide sleeve pivotable about the shaft axis to sweep the passage axis along a guide plane; and
    a guide block carried by the drive shaft, the guide block including one or more block passages dimensioned to receive a respective fixation element;
    wherein the drive shaft includes a first shaft component and a second shaft component distributed along the shaft axis;
    wherein the first shaft component is fixed to the housing relative to the shaft axis and is threadably connected to the guide block; and
    wherein the second shaft component is slidably received in a bore of the first shaft component, and the second shaft component is fixed to the guide sleeve and the guide block relative to the shaft axis.

5. The guide assembly as recited in claim 4, wherein:
    the drive shaft includes a third shaft component extending along the shaft axis; and
    the third shaft component is fixed to the guide sleeve and is slidably received in a bore extending through a wall of the housing.

6. The guide assembly as recited in claim 1, wherein the instrument establishes a resection in bone at a position spaced apart from a joint in response to moving the instrument along the guide plane.

7. A guide assembly for an orthopaedic procedure comprising:
    a housing dimensioned to contact tissue, the housing including a first slot extending along a slot axis;
    a carrier translatable along the slot axis; and
    a guide sleeve pivotably coupled to the carrier, the guide sleeve including a guide passage dimensioned to receive an instrument, wherein the guide passage extends along a passage axis, and the passage axis extends through the first slot.

8. The guide assembly as recited in claim 7, further comprising a lock mechanism including a pivot pin and a locking arm, wherein:
    the pivot pin is received in a first bore of the carrier and a second bore of the guide sleeve, and the guide sleeve is pivotable about a pivot axis of the pivot pin; and
    the locking arm includes a cam portion pivotably coupled to the pivot pin, the cam portion is rotatable between an unlocked position and a locked position to move the pivot pin along the pivot axis such that the guide sleeve binds against the housing to oppose relative movement.

9. A guide assembly for an orthopaedic procedure comprising:
    a housing dimensioned to contact tissue, the housing including a first slot extending along a slot axis;
    a carrier translatable along the slot axis;

a guide sleeve pivotably coupled to the carrier, the guide sleeve including a guide passage dimensioned to receive an instrument; and a lock mechanism including a pivot pin and a locking arm;

wherein the pivot pin is received in a first bore of the carrier and a second bore of the guide sleeve, and the guide sleeve is pivotable about a pivot axis of the pivot pin; and wherein the locking arm includes a cam portion pivotably coupled to the pivot pin, the cam portion is rotatable between an unlocked position and a locked position to move the pivot pin along the pivot axis such that the guide sleeve binds against the housing to oppose relative movement;

wherein the housing includes a second slot extending outwardly from the first slot; and wherein the pivot pin is translatable along the second slot to set a position of the carrier relative to the slot axis.

10. A guide system for preparation of a surgical site comprising:

a cutting guide comprising:
a first housing dimensioned to contact tissue;
a drive shaft coupled to the first housing, the drive shaft extending along a shaft axis; and
a first guide sleeve carried by the drive shaft, the first guide sleeve including a first guide passage extending along a passage axis and dimensioned to receive a cutting instrument, the first guide sleeve translatable along the shaft axis in response to rotation of the drive shaft, and the first guide sleeve pivotable about the shaft axis to sweep the passage axis along a guide plane; and a targeting guide comprising:
a second housing dimensioned to contact tissue; a carrier captured in the second housing; and
a second guide sleeve pivotably coupled to the carrier, the second guide sleeve including a second guide passage dimensioned to receive a guide element insertable in bone; and
a lock mechanism having a pivot pin and a locking arm;
wherein the second guide sleeve is pivotable about a pivot axis of the pivot pin, the locking arm includes a cam portion pivotably coupled to the pivot pin, and the cam portion is rotatable to cause the pivot pin and the carrier to translate along the pivot axis such that the second guide sleeve binds against the second housing.

11. The guide system as recited in claim 10, wherein:
the first housing includes a first set of fixation passages, the second housing includes a second set of fixation passages, the first and second sets of fixation passages are dimensioned to receive a common set of fixation elements insertable in bone.

12. The guide system as recited in claim 11, wherein:
the first set of fixation passages are arranged in a first spatial relationship, and the second set of fixation passages are arranged in a second spatial relationship substantially corresponding to the first spatial relationship.

13. The guide system as recited in claim 12, wherein:
the cutting guide includes a guide block carried by the drive shaft, and the guide block includes a block passage dimensioned to receive a fixation element insertable in bone.

14. A method of performing an orthopaedic procedure comprising:

positioning a cutting guide relative to a joint established by first and second bones, wherein the cutting guide comprises:
a drive shaft coupled to a first housing, the drive shaft extending along a shaft axis;
a first guide sleeve carried by the drive shaft, the first guide sleeve including a first guide passage extending along a first passage axis; and
a guide block carried by the drive shaft, and the guide block including a block passage;
setting a position of the first guide sleeve relative to the first housing, including translating the guide block and the first guide sleeve as a unit along the shaft axis in response to rotation of the drive shaft, wherein the guide block includes sidewalls dimensioned to abut walls of the first housing to limit rotation of the guide block about the shaft axis;
inserting a cutting instrument through the first guide passage;
sweeping the cutting instrument along a cutting plane to remove tissue from at least one of the first and second bones along the joint in response to pivoting the first guide sleeve about the shaft axis; and
inserting a first fixation element through the block passage and then into the first bone.

15. The method as recited in claim 14, wherein:
the first guide sleeve includes a guide slot extending along the cutting plane; and the step of positioning the cutting guide includes inserting an alignment tool
through the guide slot and then into the joint prior to the step of translating the first guide sleeve.

16. The method as recited in claim 14, wherein the first housing includes at least one fixation passage, and further comprising:
inserting a second fixation element through the at least one fixation passage and then into the second bone; and
translating the guide block along the shaft axis in response to rotating the drive shaft to cause the first and second fixation elements to compress the first and second bones against each other to establish a compressed state of the joint subsequent to the step of removing the tissue.

17. The method as recited in claim 14, wherein the first guide sleeve includes an access slot, and further comprising:
communicating a fluid stream through the access slot in a direction towards the cutting instrument.

18. The method as recited in claim 14, further comprising:
positioning a targeting guide relative to the joint subsequent to the step of
removing the tissue, wherein the targeting guide comprises: a carrier coupled to a second housing; and
a second guide sleeve pivotably coupled to the carrier at a pivot pin, the second guide sleeve including a second guide passage;
setting a position of the second guide passage relative to the second housing, including translating the carrier relative to the second housing and pivoting the second guide sleeve about a pivot axis of the pivot pin;
inserting a guide element through the second guide passage and then across the joint; and
moving a fastener along the guide element and then across the joint to fix a position of the first bone and the second bone relative to each other.

19. The method as recited in claim 18, wherein:
the step of setting the position of the second guide passage includes translating the pivot pin along the pivot axis to cause the second guide sleeve to bind against the second housing in response to rotating a locking arm coupled to the pivot pin.

20. The method as recited in claim 18, wherein the first housing includes a first set of fixation passages, and further comprising:
    inserting a second fixation element through a fixation passage of the first set of the fixation passages and then into the second bone; and
    translating the guide block along the shaft axis in response to rotation of the drive shaft to cause the first and second fixation elements to compress the first and second bones against each other to establish a compressed state of the joint.

21. The method as recited in claim 20, further comprising:
    inserting a third fixation element through another fixation passage of the first set of fixation passages and then into the first bone in the compressed state;
    removing the first fixation element from the guide block subsequent to the step of establishing the compressed state of the joint;
    removing the cutting guide from the second fixation element and the third fixation element;
    wherein the step of positioning the targeting guide includes substantially reestablishing the compressed state of the joint in response to inserting the second fixation element and the third fixation element through a second set of fixation passages of the second housing; and
    wherein the step of inserting the guide element across the joint occurs subsequent to the step of substantially reestablishing the compressed state of the joint.

22. The method as recited in claim 14, wherein the joint is a tarsometatarsal (TMT) joint.

* * * * *